(12) United States Patent
Helmer

(10) Patent No.: US 12,274,870 B2
(45) Date of Patent: Apr. 15, 2025

(54) OPTICAL CONFIGURATION OF A MEDICAMENT RESERVOIR OF A DRUG DELIVERY DEVICE

(71) Applicant: Sanofi, Paris (FR)

(72) Inventor: Michael Helmer, Frankfurt am Main (DE)

(73) Assignee: Sanofi, Paris (FR)

( * ) Notice: Subject to any disclaimer, the term of this patent is extended or adjusted under 35 U.S.C. 154(b) by 794 days.

(21) Appl. No.: 17/298,760

(22) PCT Filed: Dec. 17, 2019

(86) PCT No.: PCT/EP2019/085540
§ 371 (c)(1),
(2) Date: Jun. 1, 2021

(87) PCT Pub. No.: WO2020/127191
PCT Pub. Date: Jun. 25, 2020

(65) Prior Publication Data
US 2022/0031956 A1  Feb. 3, 2022

(30) Foreign Application Priority Data
Dec. 19, 2018 (EP) ................................. 18306737

(51) Int. Cl.
*A61M 5/31* (2006.01)
*A61M 5/315* (2006.01)

(52) U.S. Cl.
CPC ...... *A61M 5/31568* (2013.01); *A61M 5/3129* (2013.01); *A61M 2205/3306* (2013.01); *A61M 2205/3379* (2013.01); *A61M 2205/50* (2013.01)

(58) Field of Classification Search
CPC ............ A61M 5/31568; A61M 5/3129; A61M 2205/33; A61M 2205/3306;
(Continued)

(56) References Cited

U.S. PATENT DOCUMENTS

| 6,065,270 A | * | 5/2000 | Reinhard | .............. B65B 7/2821 53/140 |
| 2005/0051466 A1 | * | 3/2005 | Carter | ................... G01N 15/05 210/512.1 |

(Continued)

FOREIGN PATENT DOCUMENTS

| EP | 2716313 | 4/2014 |
| JP | 2017-523848 A | 8/2017 |

(Continued)

OTHER PUBLICATIONS

PCT International Search Report and Written Opinion in International Appln No. PCT/EP2019/085540, dated Feb. 7, 2020, 11 pages.

(Continued)

*Primary Examiner* — Shefali D Patel
*Assistant Examiner* — William R Frehe
(74) *Attorney, Agent, or Firm* — Fish & Richardson P.C.

(57) ABSTRACT

Implementations of a present disclosure are directed to a drug delivery device including a reservoir, a stopper, and a light emitting-detecting system. The reservoir includes a wall defining a proximal end and a distal end. The stopper includes an optically reflecting element. The stopper is configured to expel a portion of a medicament stored within the reservoir by moving within the reservoir in a direction from the distal end to the proximal end, such that a stopper position is indicative of an amount of the medicament within the reservoir. A light emitting system of the light emitting-detecting system is configured to provide a light signal towards the stopper from the distal end. A light detecting system of the light emitting-detecting system is configured to detect a reflected light signal provided by a reflection of the light signal on the optically reflecting element of the (Continued)

stopper and to provide an electric signal in response to detecting the reflected light signal.

18 Claims, 17 Drawing Sheets

(58) Field of Classification Search
CPC .. A61M 2205/3379; A61M 2205/3389; A61M 5/31511; A61M 2205/3553; A61M 2205/50; A61M 2205/331; A61M 2205/3313
See application file for complete search history.

(56) References Cited

U.S. PATENT DOCUMENTS

| | | | |
|---|---|---|---|
| 2013/0197445 A1* | 8/2013 | Schabbach | G16H 30/20 604/189 |
| 2013/0226134 A1* | 8/2013 | Schabbach | A61M 5/3129 604/67 |
| 2015/0174342 A1 | 6/2015 | Mitrosky et al. | |
| 2017/0246399 A1* | 8/2017 | Forlani | A61M 5/20 |
| 2019/0054252 A1* | 2/2019 | Amschler | A61M 5/24 |
| 2020/0230325 A1* | 7/2020 | Bengtsson | A61M 5/31568 |

FOREIGN PATENT DOCUMENTS

| | | |
|---|---|---|
| WO | WO 2016/036574 | 3/2016 |
| WO | WO 2017/013463 A1 | 1/2017 |
| WO | WO 2017/013464 A1 | 1/2017 |
| WO | WO 2018/138542 A1 | 8/2018 |
| WO | WO 2018/202663 | 11/2018 |
| WO | WO 2018/224460 | 12/2018 |
| WO | WO 2019/175790 A1 | 9/2019 |
| WO | WO 2020/217076 A1 | 10/2020 |
| WO | WO 2020/217094 A1 | 10/2020 |
| WO | WO 2021/220024 A1 | 11/2021 |
| WO | WO 2021/260404 A1 | 12/2021 |
| WO | WO 2022/079462 A1 | 4/2022 |

OTHER PUBLICATIONS

International Preliminary Report on Patentability in International Appln No. PCT/EP2019/085540, dated Jun. 16, 2021, 7 pages.

* cited by examiner

OPTICAL CONFIGURATION OF A MEDICAMENT RESERVOIR OF A DRUG DELIVERY DEVICE

CROSS-REFERNCE TO RELATED APPLICATIONS

The present application is the national stage entry of International Patent Application No. PCT/EP2019/085540, filed on Dec. 17, 2019, and claims priority to Application No. EP 18306737.0, filed on Dec. 19, 2018, the disclosures of which are incorporated herein by reference.

TECHNICAL FIELD

This disclosure relates to a drug delivery device, and more particularly, to an optical configuration of a medicament reservoir of the drug delivery device for sensing a quantity of a medicament stored within the medicament reservoir and a sealing of the medicament reservoir.

BACKGROUND

Some diseases are treatable by a regular injection of a particular dose of a medicament. Such injections can be performed by using drug delivery devices, which are applied either by medical personnel or by patients themselves. For instance, pre-filled disposable pens can be used as drug delivery devices. Alternatively, re-usable pens having medicaments stored in removable cartridges can be used. Re-usable pens allow replacement of an empty medicament cartridge by a new one.

In some devices, the medicament dose to be injected can be manually selected at the pen by turning a dosage knob and observing the actual dose from a dosage window or display of the medicament pen. In other devices, such as auto-injectors, the entire volume of the cartridge (or pre-filled syringe) is injected into the body, so that selecting a dose is not necessary. To monitor medicament injection, for instance to prevent false or incorrect handling of the drug delivery device, to keep track of the doses already applied (for instance, in the case of multi-dose pens) or to keep track of whether the entire dose has been administered (for instance, in the case of auto-injectors), it is desirable to measure information related to a feature and/or use of the drug delivery device. For example, treatment can be optimized by detecting one or more of the injected medicament types, doses, and timings of the injection in a reliable and accurate manner and sharing the data with remote devices.

SUMMARY

Implementations of the present disclosure include drug delivery devices configured for optically detecting medicament fluid amounts and sharing detected data in a healthcare continuum. In accordance with one aspect of the present invention, a drug delivery device includes a reservoir, a stopper, a light emitting system, and a light detection system. The reservoir includes a wall defining a proximal end and a distal end. The stopper includes an optically reflecting element, the stopper is configured to expel a portion of a medicament stored within the reservoir by moving within the reservoir in a direction from the distal end to the proximal end, such that a stopper position is indicative of an amount of the medicament within the reservoir. The light emitting system is configured to provide a light signal towards the stopper from the distal end. The light detection system is configured to detect a reflected light signal provided by a reflection of at least a portion of the light signal on the optically reflecting element of the stopper, the reflected light signal travelling towards the distal end that travelled through a second portion of the wall of the reservoir, the light detector configured to provide an electric signal in response to detecting the reflected light signal.

In some implementations, the light signal is configured to travel through a first portion of the wall of the reservoir and wherein the reflected light signal is configured to travel through a second portion of the wall of the reservoir. In some implementations, the light signal is configured to travel through a first portion of the wall of the reservoir and wherein the reflected light signal is configured to travel through a second portion of the wall of the reservoir, at least one of the first portion of the wall and the second portion of the wall being opposite to an inner face of the stopper. In some implementations, at least one of the first portion of the wall and the second portion of the wall at the proximal end is substantially optically transparent. In some implementations, the light emitting system is configured to emit the light signal towards a central portion of the stopper. In some implementations, at least one of the first portion of the wall and the second portion of the wall defines at least one of a planar horizontal geometry and a planar oblique geometry. In some implementations, at least one of the first portion of the wall and the second portion of the wall defines at least one of a convex geometry and a concave geometry. In some implementations, the light emitting system comprises a light emitting diode and the light detection system comprises a light dependent resistor configured to emit the electrical signal based on a brightness of the reflected light signal. In some implementations, the light emitting system comprises a laser diode and the light detection system comprises a laser receiver sensor configured to emit the electrical signal based on an angle or a phase of the reflected light signal. In some implementations, the light detection system comprises a concave lens. In some implementations, the optically reflecting element is located within a central portion of the stopper. In some implementations, the optically reflecting element comprises one of a cylinder lens and an aspherical lens. In some implementations, the drug delivery device includes a processor that is configured to process the electric signal to determine the amount of the medicament within the reservoir. In some implementations, the processor is configured to process the electric signal to determine a property of the medicament within the reservoir. In some implementations, the medicament reservoir is made of an optically transparent plastic material, preferably including one of a cyclic olefin copolymer (COC) and a cyclo-olefin polymer (COP). In some implementations, the emitting system and detection system can be arranged to emit and receive light perpendicular to a travelling direction of the stopper.

In accordance with another aspect of the present invention, a drug delivery system includes: a drug delivery device, a transmitter and an external device. The drug delivery device includes a reservoir, a stopper, a light emitting system, and a light detection system. The reservoir includes a wall defining a proximal end and a distal end. The stopper includes an optically reflecting element, the stopper is configured to expel a portion of a medicament stored within the reservoir by moving within the reservoir in a direction from the distal end to the proximal end, such that a stopper position is indicative of an amount of the medicament within the reservoir. The light emitting system is configured to provide a light signal towards the stopper from the distal end. The light detection system is configured to detect a reflected light signal provided by a reflection of at least a portion of the light signal on the optically reflecting element of the stopper, the reflected light signal travelling towards the distal end that travelled through a second portion of the wall of the reservoir, the light detector configured to provide an electric signal in response to detecting the reflected light signal. The transmitter is configured to transmit the injection device data. The external device includes: a receiver configured to receive the injection device data, and one or more processors configured to process the injection device data and to generate result data.

It is appreciated that systems in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more embodiments of the present disclosure are set forth in the accompanying drawings and the description below. Other features and advantages of the present disclosure will be apparent from the description and drawings, and from the claims.

BRIEF DESCRIPTION OF THE FIGURES

Like reference symbols in the various drawings indicate like elements.

DETAILED DESCRIPTION

Implementations of the present disclosure are generally directed to using an optical system to determine an amount of medicament within a drug delivery device during the operation of the drug delivery device and transmitting the determined data. The optical system includes a stopper that moves when medicament is dispensed and that has an optically reflecting element, a light source that emits a light signal towards the stopper, and a light detector that detects a reflection from the optically reflecting element of the stopper. The detected light signal can be processed to determine the position of the stopper before, during, and/or after a medicament is expelled from the medicament reservoir. Subsequently, the amount of medicament within the drug delivery device can be determined.

Drug delivery devices configured to determine the amount of the fluid (e.g., medicament) within the drug delivery device before, during or after the operation of the drug delivery device can support medical treatments and facilitate sharing of medical data. For example, a healthcare provider may optimize healthcare treatment by avoiding usage of expired or incorrectly stored medicaments and by avoiding shortage of medical supply based on monitoring a plurality of parameters associated with the medicament. The medicament data, for example, the amount of medicament that is contained within the drug delivery devices and delivered by the drug delivery devices, can be shared with one or more healthcare providers and other entities within a healthcare continuum (e.g., a system that supports, guides, and tracks medical treatment of patients over time through a comprehensive array of health services spanning all levels and intensity of care) that may use the information (e.g., to replenish the medical supply).

FIGS. 1A-1G illustrate a system 100 that can be used to determine the amount of medicament within an example drug delivery device 102 and, in some implementations, share the data with an external device 150. FIGS. 1A-1G include exploded views of the example drug delivery device 102 including different types of medicament amount detection systems 103 that can be used to determine the amount of medicament within the drug delivery device 102 (e.g., using a light emitting system, a light detection system and a reflecting stopper, described in greater detail below). In some examples, the drug delivery device 102 can be a pen device (FIGS. 1A, 1B, and 1G) including a medicament container, such as, for instance, a cartridge having an attachable needle or a pre-filled syringe having a staked needle (FIG. 1C-1F). In one aspect, the pen device can be a pre-filled, disposable injection pen or a reusable injection pen.

Figure 1A:
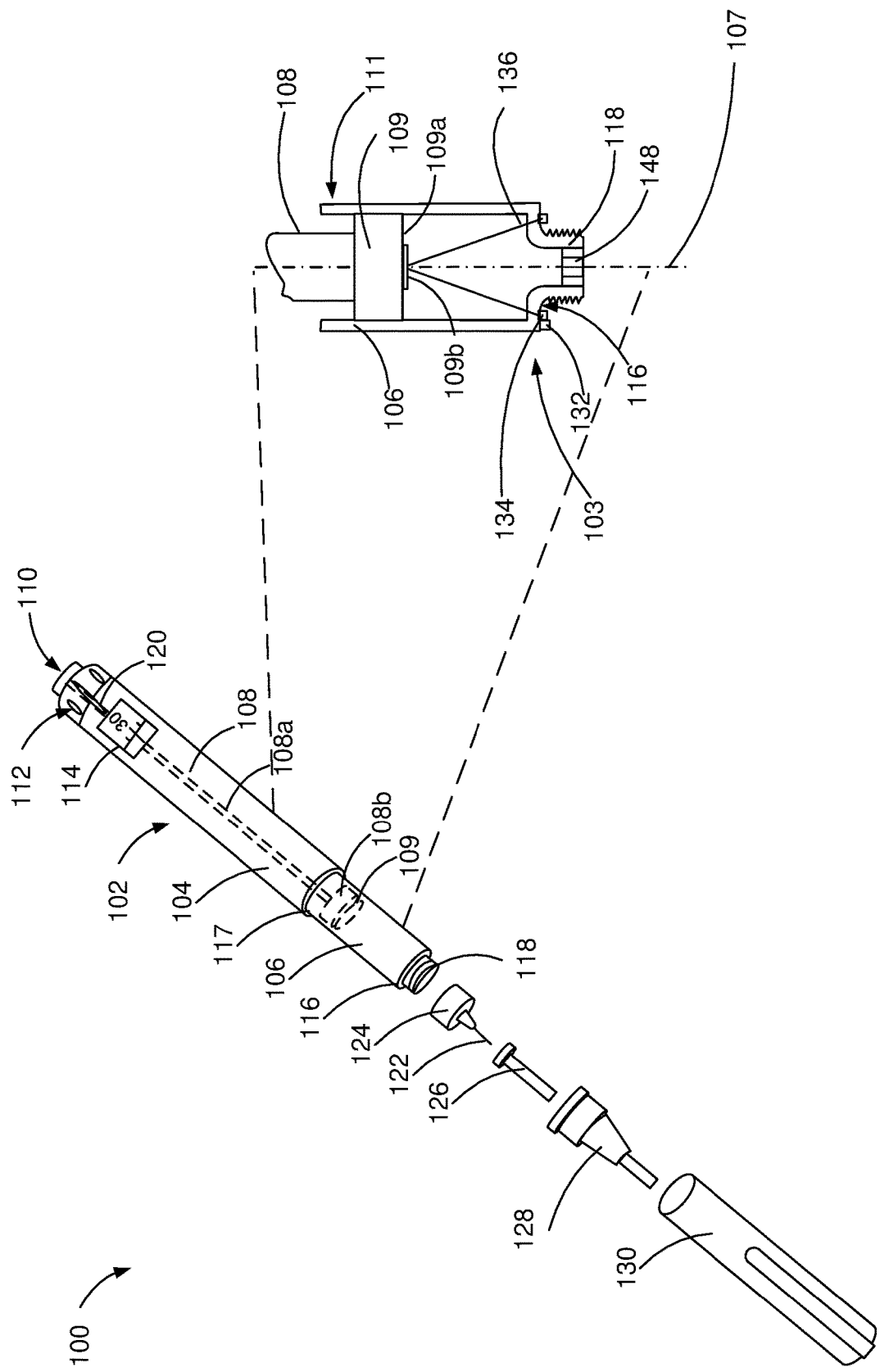
FIGS. 1A-1G are exploded views of examples of devices in accordance with the present disclosure.
Figure 1B:
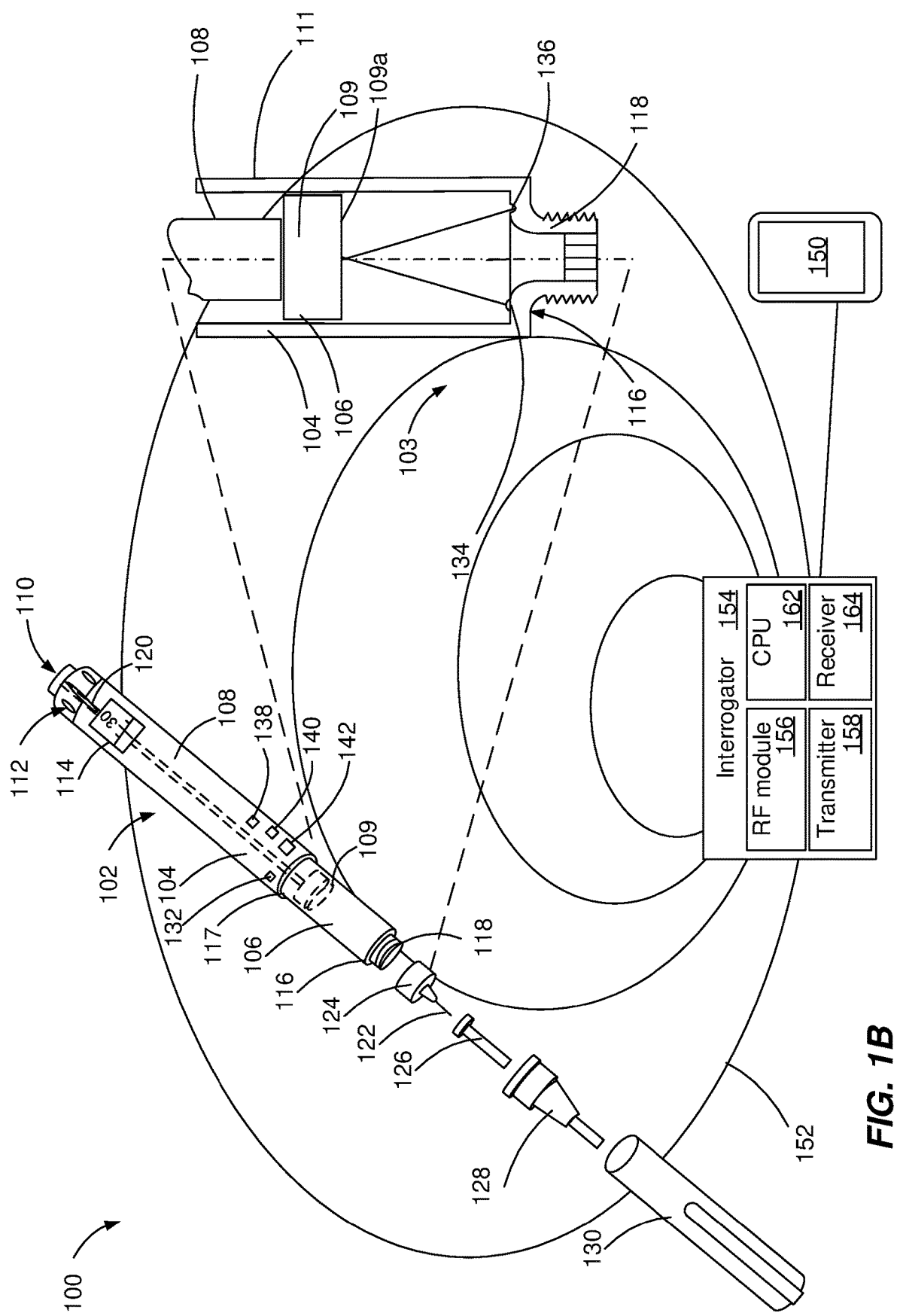
Figure 1C:
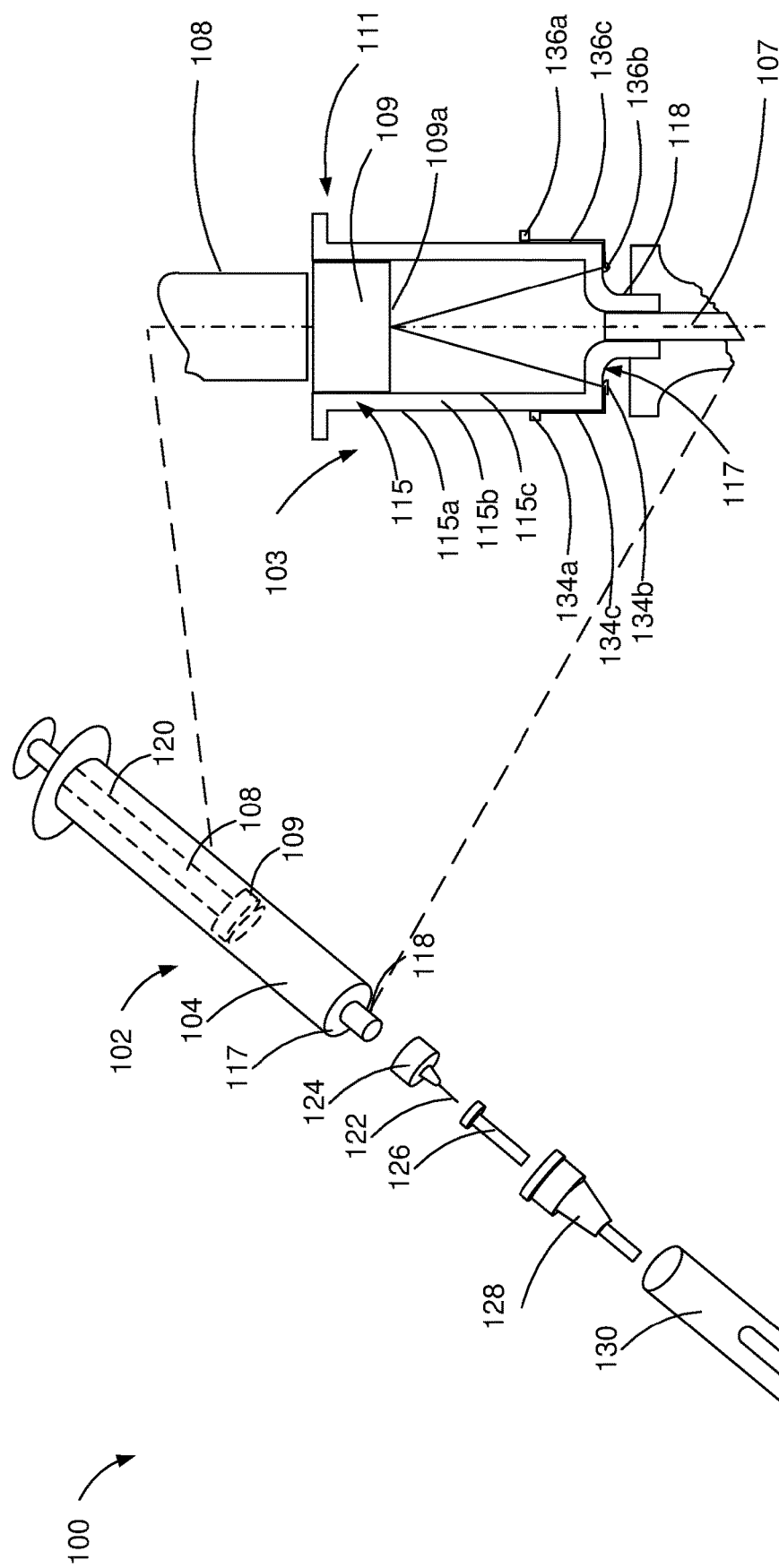
Figure 1D:
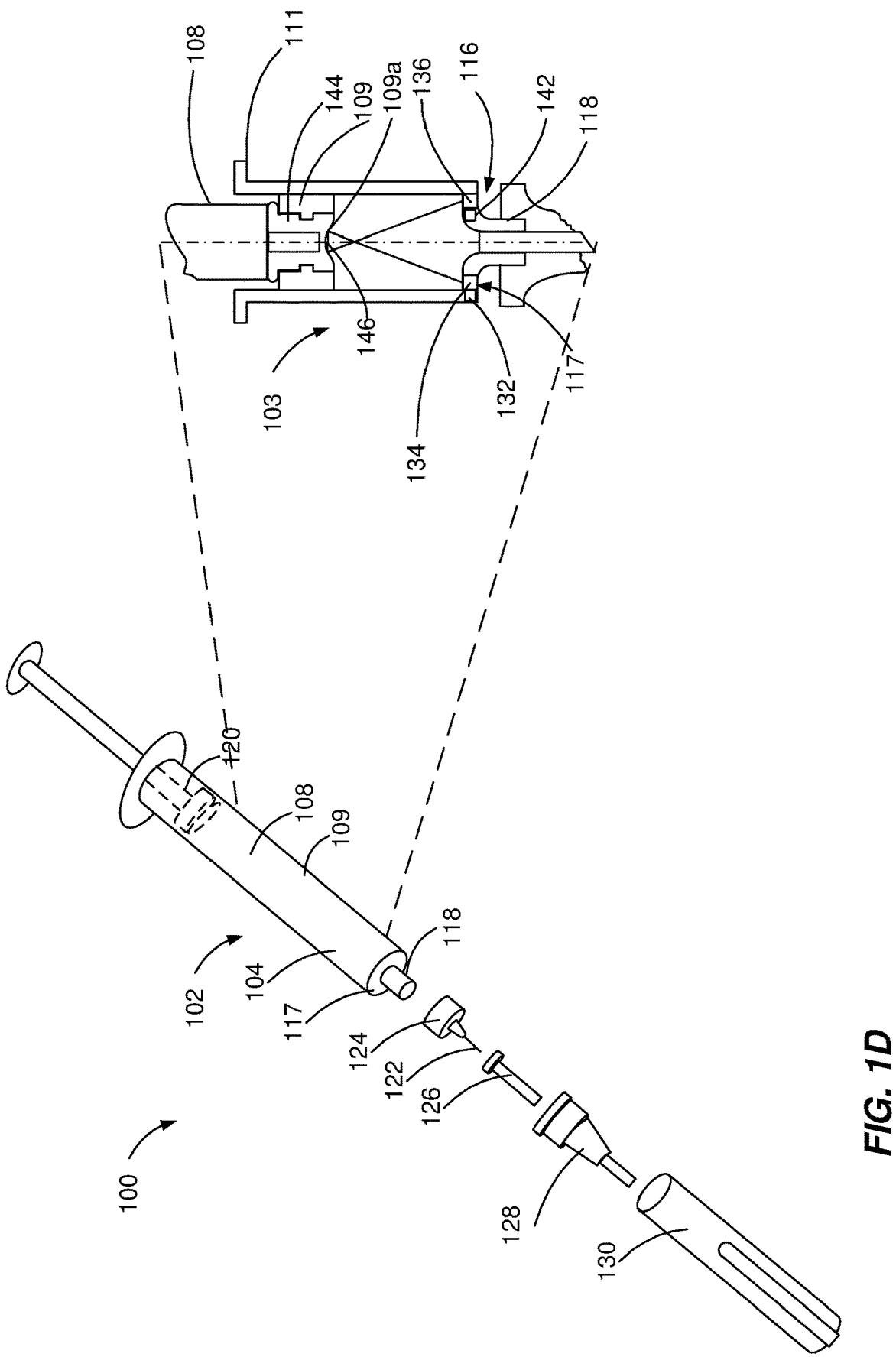
Figure 1E:
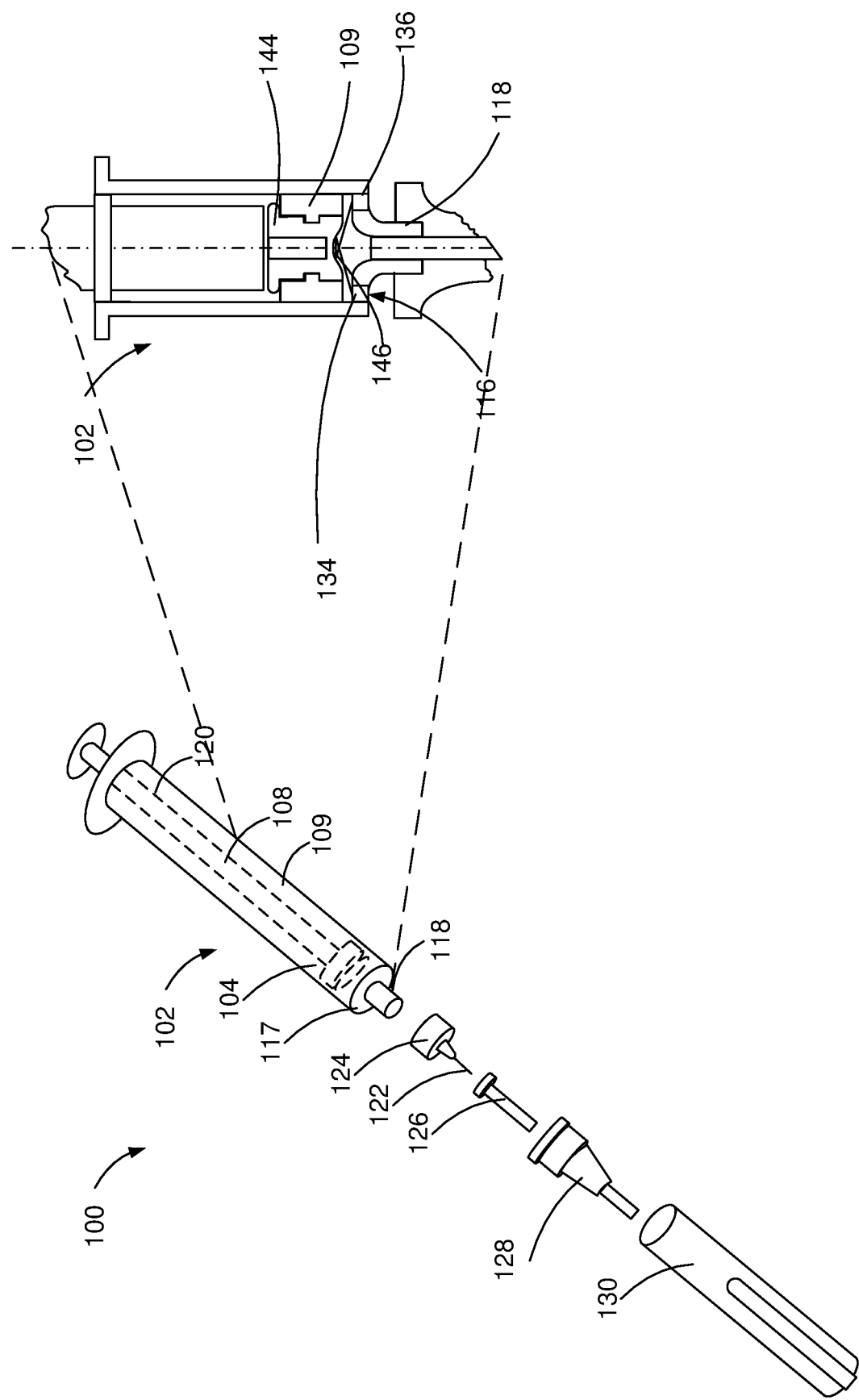
Figure 1F:
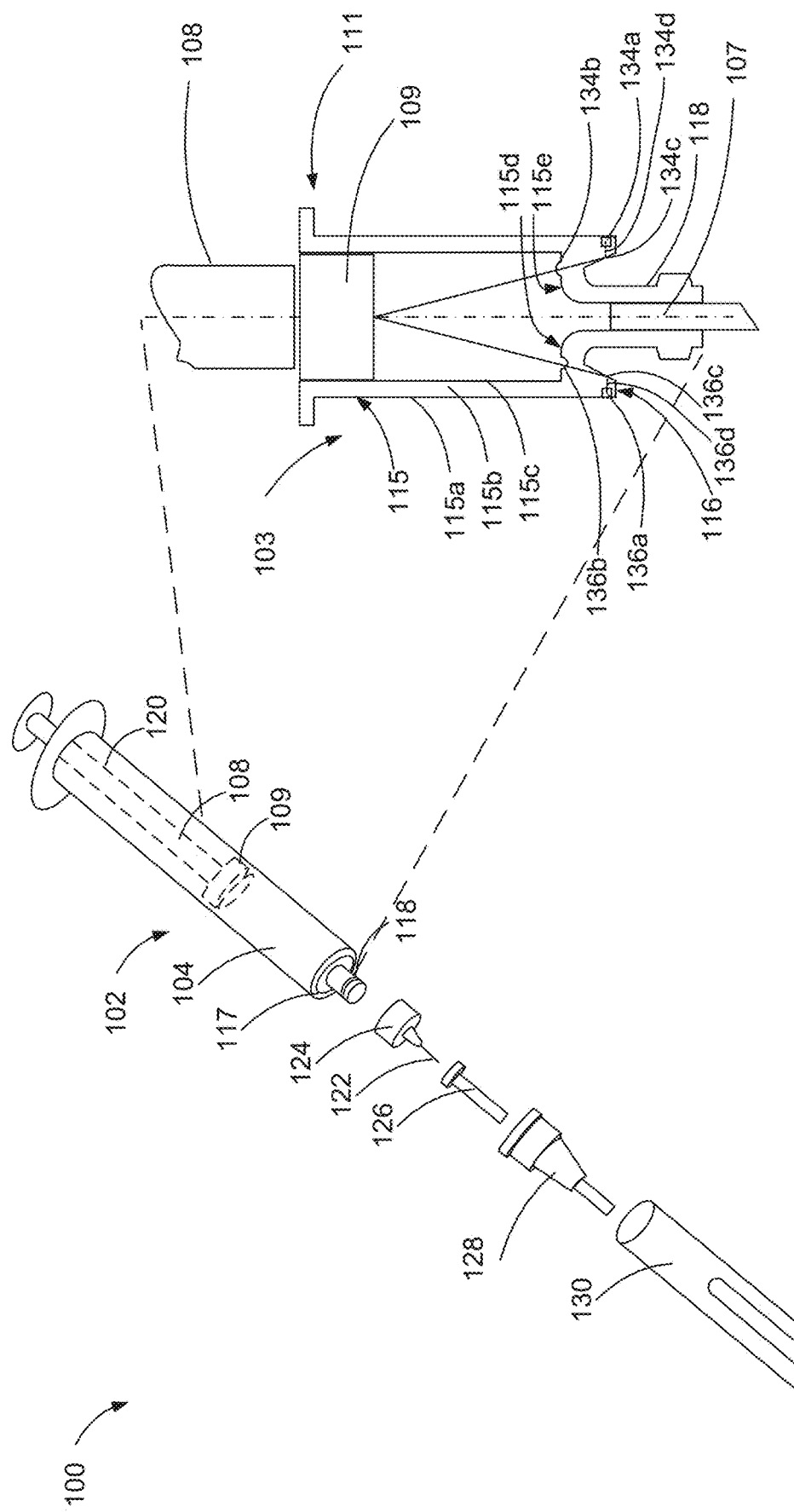
Figure 1G:
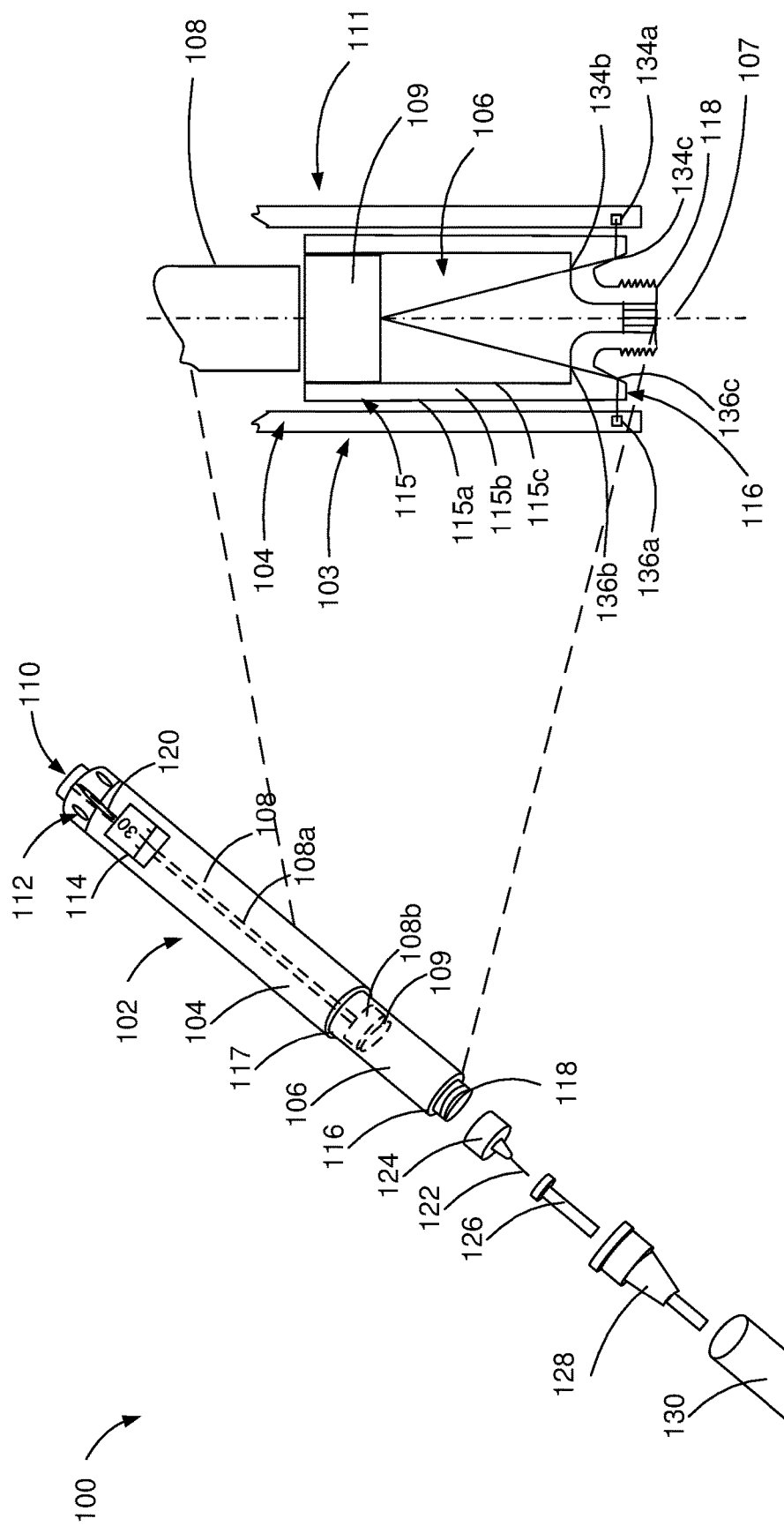

In one aspect, the pen device may be used to deliver only one injection (administering the entire contents of the medicament container). In another aspect, the pen device may be used to deliver multiple injections (administering only a part of the contents of the medicament container). FIGS. 1A, 1B, and 1G illustrate a variable-dose pen device 102 and FIGS. 1C to 1E illustrate a syringe-type device 102. Even though each of the drug delivery devices 102 in FIGS. 1A to 1G is illustrated in combination with a particular type of medicament amount detection system 103, it is understood that each type of medicament amount detection system 103 can be implemented in any type of drug delivery device 102. In one aspect, the drug delivery device 102 includes a housing 104 and a medicament reservoir 106. In one aspect, medicament reservoir 106 may comprise a cartridge or a pre-filled syringe. In an aspect, drug delivery device 102 may comprise a plunger 108. In one aspect, drug delivery device 102 may optionally comprise an injection button 110. In one aspect, drug delivery device 102 may optionally comprise a dosage knob 112. In one aspect, drug delivery device 102 may optionally comprise a dosage window 114.

In one aspect, housing 104 can include a wall 115 configured to define a medicament container or contain a medicament reservoir 106 including a wall 115 that can store an amount of medicament. The wall 115 can include an outer flange 115a, a core 115b, and an inner flange 115c. In one aspect, the geometry of wall 115 may be configured as needed. In one aspect, component materials of wall 115 may be configured. Configuring the geometry and/or component materials of wall 115 may enable one or more functionalities of the medicament amount detection system 103.

In an aspect, the geometry and/or composition materials of the wall 115 can enable transmission, internal reflection, external reflection, and/or refraction of light beams. For example, the end portion 117 of the wall 115 and/or the end portion 116 of the wall 115 can include a substantially planar horizontal (FIGS. 1A-1G) that enables transmission of light beams and/or a substantially planar oblique surface that enables reflection of a light beam (FIGS. 1F and 1G). The portion of the wall 115 between the distal end 111 and the proximal end 116, 117 can have a tubular (cylindrical) shape. At least a portion of the housing 104 and/or the medicament reservoir 106 are made of materials that are optically transparent for light beams in visible and infrared spectrum to enable functionality of the optical components (light emitting system 134 and light detection system 136) if they are attached to the outer flange 115a of the wall 115.

In one aspect, the composition materials of the housing 104 and/or the medicament reservoir 106 can include glass and/or an optically transparent plastic material, such as (preferably) any of cyclic olefin copolymer (COC), cyclo-olefin polymer (COP). The composition materials can be configured to have a high double refraction (e.g., optical refractive index higher than 1.5), to provide a high moisture barrier (e.g., moisture absorption smaller than 0.01) and a good material strength (e.g., a charpy impact strength of about 13 to 15). For example, plastic materials, such as COC materials include high purity, high moisture barrier, excellent double refraction, breakage prevention, and low density. Most COC grades can undergo sterilization by gamma radiation, by high temperature steam, or by ethylene oxide. COC also has a very low energy and a nonreactive surface, which can extend shelf life and purity of medications, such as insulin and other protein drugs, stored in medicament reservoirs 106 (e.g., vials, reservoir of syringes and cartridges).

The medicament reservoir 106 (container) can include a wall 115 configured to contain a fluid medicament. The medicament can include a pharmaceutical formulation containing at least one pharmaceutically active compound. The medicament can include insulin analogs, insulin derivatives, analgesics, hormones, beta agonists, corticosteroids, or a combination of any of the above-mentioned drugs. The medicament can be optically transparent so that it does not affect a functionality (e.g., light transmission) of the medicament amount detection system 103. The medicament reservoir 106 can include a sealing component 148 and an aperture 149, which are described in detail with reference to FIGS. 2A-2F.

The plunger 108 can be configured to expel a portion of the medicament contained within the medicament reservoir 106. The plunger 108 can include a plunger rod 108a and a plunger head 108b configured to push a stopper 109. The stopper 109 can be configured to expel a portion of a medicament stored within the medicament reservoir 106 by moving within a tubular wall 115 of the medicament reservoir 106 in a direction from the distal end 111 to the proximal end 116, 117, such that a position of the stopper 109 is indicative of an amount of the medicament within the medicament reservoir 106. The terms "proximal," "proximally" and "proximal end" refer to the end of a drug delivery device towards which the stopper is travelling during administration of the medicament. The terms "distal," "distally" and "distal end" refer to the end of the drug delivery device that is opposite to the "proximal end".

At least a portion of the stopper 109 can be configured to be optically reflective. For example, a portion of a surface 109a of the stopper 109 of the plunger 108 can include an optically reflecting element, such as an optical coating 109b deposited at a particular location (e.g., a central section) of the surface 109a (FIG. 1A). As another example, the entire surface of the stopper 109a can be configured to be optically reflecting FIGS. 1B, 1C, 1F, and 1G). As another example, the surface 109a of the stopper 109 can include an optically reflecting element, such as a reflective lens 146 (FIGS. 1D and 1E). A portion (e.g., at least 90%) of the surface of the stopper 109 that is in contact with the medicament can be configured to be planar to minimize the dead filling volume of the drug delivery device 102.

In one aspect, a position of the stopper 109 can be associated with an amount of the medicament within the drug delivery device 102. Any of the described and illustrated configurations of the stopper 109 can be applied to any type of injection devices 102, such as cartridges and pre-filled syringes alike. For instance, stopper 109 is pictured as a mere block in FIGS. 1A, 1B, 1C, 1F, and 1G. Stopper 109 is pictured having additional structure in FIGS. 1D and 1E. Nonetheless, it is understood that each of the stoppers pictured in FIGS. 1A, 1B, 1C, 1F, and 1G may also be used with the systems shown in FIGS. 1D and 1E. In a similar manner, it is understood that each of the stoppers pictured in FIGS. 1D and 1E may also be used with the systems shown in FIGS. 1A, 1B, 1C, 1F, and 1G.

For some pen devices, notably for pen devices configured to deliver multiple doses, a dose of the contained medicament can be ejected from the drug delivery device 102 by turning the dosage knob 112, and the selected dose is then displayed via dosage window 114, for instance in multiples of so-called International Units (IU), wherein one IU is the biological equivalent of about 45.5 micrograms of pure crystalline medicament (1/22 mg). It is however understood that the present disclosure also covers injection pens, where the user cannot freely select the dose to administer, but where the dose is fixed (so-called "fixed-dose" devices). An example of a selected dose displayed in dosage window 114 may for instance be 30 IUs, as shown in FIGS. 1A and 1B. In some implementations, the selected dose can be displayed differently, for instance by an electronic display.

In one aspect, turning the dosage knob 112 can cause a mechanical click sound to provide acoustic feedback to a user. The numbers displayed in dosage window 114 can be printed on a sleeve that is contained in housing 104 and mechanically interacts with a plunger 108 in medicament reservoir 106. For syringes, a dose of the contained medicament can be ejected from the drug delivery device 102 by directly applying pressure on the plunger, as shown in FIGS. 1D and 1E. It is understood that the present disclosure also covers autoinjectors, where the entire contents of the medicament container are being administered automatically. In that case, in one aspect, the optical system may serve to monitor whether the stopper has indeed travelled the expected distance (for instance, the entire distance) within the medicament container.

In one aspect, housing 104 can be attached to a needle 122 using the handle 124. The needle 122 is protected by an inner needle cap 126 and an outer needle cap 128, which in turn can be covered by a cap 130. When needle 122 can be inserted into a skin portion of a patient, and then injection button 110 is pushed, the medicament dose displayed in display window 120 is ejected from the drug delivery device 102. When the needle 122 of drug delivery device 102 remains for a certain time in the skin portion after the injection button 110 is pushed, a high percentage of the dose is actually injected into the patient's body. Ejection of the medicament dose can generate a mechanical click sound, which can be different from the sounds produced when using dosage knob 112. It is however understood that the present disclosure is not limited to cartridges with attachable needle assemblies. In another aspect, pre-filled syringes with staked needles may also be used.

In one aspect, drug delivery device 102 can be used for several injection processes until either the medicament reservoir 106 is empty or the expiration date of drug delivery device 102 (e.g. 28 days after the first use) is reached. It is understood however that the present disclosure also covers systems where drug delivery device 102 is an autoinjector that delivers its entire dose in a single injection process. When using a multiple-dose injection device, before using drug delivery device 102 for the first time, it can be necessary to perform a so-called "prime shot" to remove air from medicament reservoir 106 and needle 122, for instance by selecting two units of medicament and pressing injection button 110 while holding drug delivery device 102 with the needle 122 upwards.

In one aspect, the medicament amount detection system 103 may comprise an optical system configured to monitor a change in the amount of medicament that is contained within the drug delivery device 102 in order to thereby derive an amount of medicament delivered by the drug delivery device 102. Monitoring includes generation of a light signal and detection of a reflected signal to determine the position of the stopper 109 before and after each injection. In another example, monitoring may also include generation of a light signal and detection of a reflected signal to determine the position of the stopper 109 before and after each second, third, fourth, etc. injection in order to determine an average expelled dose.

In one aspect, a processor can be configured to compare the detected position information/data and calculate an amount of medication that is remaining in the medicament reservoir 106. In some implementations, the processor can be configured to calculate the amount of medication that has been ejected from the medicament reservoir 106. Monitoring is performed throughout the lifetime of the medicament reservoir 106 and/or the drug delivery device 102, and, preferably, during the operation of the drug delivery device 102. For example, the monitoring is performed each time a medicament is expelled by the drug delivery device 102.

In some implementations, the medicament amount detection system 103 can be associated with an identifier. The identifier can be a random number r that can be encoded in a machine-readable medium, such as radio frequency identification (RFID) data, in a 2-dimensional (2D) bar code, and/or in a QR code included with the drug delivery device. The random number r can be associated with the medicament amount detection system 103 and can be used to uniquely identify the medicament amount detection system 103 and corresponding drug delivery device-level data stored in a repository.

In one aspect, the medicament amount detection system 103 can include a power source 132, a light emitting system 134, a light detection system 136, and a processor 138. In some implementations, the medicament amount detection system 103 can include an antenna 140 and a sensor 142. In some implementations, the power source 132 is integrated in the light emitting system 134. The power source 132 can be an integrated battery or a super capacitor. In some implementations, the power source 132 can include an energy harvester configured to harvest energy from interrogation signals emitted by the external device 150 or mechanical energy generated by an interaction of a user with the drug delivery device 102. The power source 132 can be configured to supply energy to the components of the medicament amount detection system 103 continuously or under particular conditions (e.g., when the drug delivery device 102 is within a near-field communication (NFC) field 152). In some implementations, the processor 138 is integrated in the light detection system 136.

In one aspect, the light emitting system 134 can include a light source 134a, a light emitting element 134b, and a coupling element 134c. The light source 134a can include one or more light emitting diodes (LEDS) or laser diodes. In some implementations, the light source 134a can emit an invisible light signal (e.g., in infrared spectrum). In some implementations, the wavelength of the light generated by the light source 134a depends on the medicament to be expelled by the drug delivery device 102. For example, the light source 134a can be configured to emit a light signal at a particular wavelength that does not affect the pharmacological properties of the medicament. The light source 134a can be attached to the outer flange 115a of the wall 115, the inner flange 115c of the wall 115 or within the core 115b of the wall 115 or it can be separated from the wall 115 of the medicament reservoir 106 (e.g., attached to the wall of the housing 104 of the drug delivery device 102, as illustrated in FIG. 1G).

In one aspect, the light source 134a can be attached to or inserted in a portion of the proximal end 117 of a wall 115 of the housing 104 or a portion of the proximal end 116 of a wall 115 of the medicament reservoir 106 that is adjacent to the nosepiece 118. The light emitting element 134b can include optical components, such as a lens (e.g., convex or plano-convex lens) or a mirror, configured to direct the light beam in a particular direction (e.g., center of the surface of the stopper 109, as illustrated in FIGS. 1C, IF, and 1G). The light emitting element 134b can be attached to the outer flange 115a of the wall 115, the inner flange 115c of the wall 115 or within the core 115b of the wall 115 or it can be a portion of the wall 115 (e.g., a first portion 115e of the wall 115, as illustrated in FIG. 1F. or inner flange 115c, as illustrated in FIG. 1G). The light emitting element 134b can be configured to direct the light towards the stopper 109.

In one aspect, the light emitting element 134b can be configured to maximize light refraction and minimize reflection. For example, the light emitting element 134b can include an anti-reflection coating. The light emitting element 134b can be a lens with a radius selected based on the position of the light source 134a to control the incident angle. In some implementations, the light source 134a and the light emitting element 134b are integrated in a single element, as illustrated in FIGS. 1A, 1B, 1D, and 1E. In some implementations, the light source 134a and the light emitting element 134b are separate components attached to different portions of the wall 115, as illustrated in FIGS. 1C, 1F, and 1G. The light source 134a and the light emitting element 134b can be optically connected to each other by a coupling element 134c, as illustrated in FIGS. 1C, 1F, and 1G.

In one aspect, the coupling element 134c can be configured to transmit light between different optical components (e.g., light source 134a and the light emitting element 134b) and/or across the wall of the medicament reservoir 106. The coupling element 134c can include active and/or passive optical elements, such as an optical fiber or other optical transmission elements. In some implementations, the coupling element 134c can be configured to assist a light beam (e.g., with a particular wavelength) colliding with the outer flange 115a of the medicament reservoir 106 with entering the inner space of the medicament reservoir 106. For example, the light emitted by the light source 134a is directed horizontally (e.g., along portion 134d as shown in FIG. 1F) towards the substantially planar oblique portion of the wall 115. The substantially planar oblique portion of the wall 115 acts as a coupling element 134c by reflecting the light beam towards the light emitting element 134b (e.g., bulb-like element, as illustrated in FIG. 1F or substantially planar portion of the inner flange 115, as illustrated in FIG. 1G).

The light detection system 136 can include a light detector 136a, a light collector 136b, and a coupling element 136c. The light detector 136a can include one or more photodiodes, phototransistors, photomultipliers, photoresistors, laser sensors or any other device configured to convert an optical signal into an electrical signal. The light detector 136*a* can be attached to the outer flange 115*a*, to the inner flange 115*c*, or within the core 115*b* (e.g., by an outer flange 115*a*) of the medicament reservoir 106 or it can be separated from the wall of the medicament reservoir 106 (e.g., attached to the wall of the housing 104 of the drug delivery device 102, as illustrated in FIG. 1G). The light collector 136*b* can include any optical element, such as a lens (e.g., concave or plano-concave lens) or a mirror, configured to receive the light beam from a particular direction (e.g., center of the surface of the stopper 109), as illustrated in FIGS. 1C and 1F. The light collector 136*b* can be attached to the outer flange 115*a* of the wall 115, the inner flange 115*c* of the wall 115 or within the core 115*b* of the wall 115 or can be a portion of the wall 115 (e.g., a second portion 115*d* of the wall 115, as illustrated in FIG. 1F or as illustrated in FIG. 1G).

In an aspect, light collector 136*b* can be configured to maximize light refraction and minimize reflection. For example, the light collector 136*b* can include an antireflection coating. The light collector 136*b* can be a lens with a radius selected based on the position of the light detector 136*a* to control the refraction angle. In some implementations, the light detector 136*a* and the light collector 136*b* are integrated in a single element, as illustrated in FIGS. 1A, 1B, 1D, and 1E. In some implementations, the light detector 136*a* and the light collector 136*b* are separate components, as illustrated in FIGS. 1C, 1F, and 1G. The light detector 136*a* and the light collector 136*b* can be optically connected to each other by a coupling element 136*c*, as illustrated in FIGS. 1C and 1F. The coupling element 136*c* can be configured to transmit light between different optical components (e.g., light detector 136*a* and the light collector 136*b*) and/or across the wall of the medicament reservoir 106.

In an aspect, coupling element 136*c* can include active and/or passive optical elements, such as an optical fiber or other optical transmission elements. In some implementations, the coupling element 136*c* can be configured to assist a light beam (e.g., with a particular wavelength) colliding with the inner wall of the medicament reservoir 106 with existing to the outer space of the medicament reservoir 106. For example, the light reflected by the stopper 109 is directed towards the light collector 136*b* (e.g., a pit-like element, as illustrated in FIG. 1F or a substantially planar portion of the inner flange 115, as illustrated in FIG. 1G). The light collector 136*b* directs the refracted light towards a substantially planar oblique portion of the wall 115.

In an aspect, the substantially planar oblique portion of the wall 115 can act as a coupling element 134*c* to reflect the light beam (e.g., at a right angle) and direct it substantially horizontal (e.g. along portion 136*d* as shown in FIG. 1F) towards the light detector 136*a* (e.g., inserted in the core 115*c*, as illustrated in FIG. 1F or separated from the medicament reservoir 106, as illustrated in FIG. 1G). An advantage of the internal reflection on a portion of the wall 115 as illustrated in FIG. 1G, corresponds to the fact that the medicament reservoir 106 can be free of optical components (e.g., light detector 136*a* nor the light source 134*a*), such that neither the light detector 136*a* nor the light source 134*a* must be attached to/embedded in the medicament reservoir 106 (e.g., cartridge). For example, a light beam (generated outside the medicament reservoir 106 by a light source 134*a*) could enter the wall 115 at a right angle (e.g., through an optically transparent outer flange 115 or through a defined optical window).

IN an aspect, the light beam can be internally reflected by a portion of the wall 115 (acting as a coupling element 134*c*) through an optically transparent inner flange 115*c* (acting as a light emitting element 134*b*) towards the stopper 109. The light beam reflected by the stopper 109 can cross the optically transparent inner flange 115*c* (acting as a light collector 136*b*) and it can undergo a second internal reflection at the opposite side of the wall 115 (acting as a coupling element 136*c*) to then exit the wall 115, for example, at a right angle. Any medicament reservoir 106 (e.g., cartridge) (geometrically) configured to have an optical pathway (e.g., light emission, transmission, and detection) that enables direction of an outer light beam towards the stopper 109 can be implemented in the medicament reservoir 106, without any optical elements attached to or inserted in the wall of the medicament reservoir 106.

The light emitting system 134 and the light detection system 136 can be included in (or attached to) either a cartridge insertable in a pen device (FIGS. 1A and 1B) or the medicament reservoir 106 of a syringe (FIG. 1C-1F). The light emitting system 134 and the light detection system 136 can be attached to the outer wall of the medicament reservoir 106 by the proximal end 116 (FIG. 1A), 117 (FIG. 1C). The light emitting system 134 and the light detection system 136 can be completely or partially embedded in the wall portion by the proximal end 116 of the medicament reservoir 106 or proximal end 117 of the drug delivery device 102 (FIGS. 1D and 1E). In some implementations, if the light emitting system 134 and the light detection system 136 are attached to the inner wall of the medicament reservoir 106, they are covered by a protective layer to prevent contamination of the medicament stored within the medicament reservoir 106 (FIG. 1B).

In an aspect, the light emitting system 134 can be in a first position of the proximal end 116 or 117. The light detection system 136 can be in a second position in the proximal end 116 of the medicament reservoir 106 or to the wall portion 117 of the drug delivery device 102. The second position can be selected relative to the first position for optimal detection of reflected light signal. For example, the light emitting system 134 and the light detection system 136 can be arranged in parallel and spaced apart radially by a symmetrically or asymmetrical radial offset from a longitudinal axis 107 of the drug delivery device 102. In the present example, the positions of the proximal end 116 and 117 are opposite to an inner face of the stopper 109. The light emitting system 134 and light detection system 136 can be positioned such that a light beam goes from the light emitting system 134 through the medicament to the stopper 109 and reflects from the stopper 109 through the medicament to the light detection system 136. The light emitting system 134 and light detection system 136 can be positioned such that the distance between the light emitting system 134 and light detection system 136 decreases as medicament is expelled from the medicament reservoir 106.

The light emitting system 134 can be configured to emit a light signal in a direction based on the first position through the medicament towards a center of the surface of the stopper 109. As illustrated in FIG. 1A, the surface of the stopper 109 can be planar and reflective, being configured to reflect the light signal towards the light detection system 136. As illustrated in FIGS. 1D and 1E, the stopper 109 can include an insert configured to reflect the light signal towards the light detection system 136. For example, the insert 144 can include at least one of a mirror and a lens 146 (e.g., cylindrical or aspherical lens) that guides the laser beam towards the light detection system 136.

In some implementations, the electrical signal generated by the light detection system 136 is transmitted to the processor 138, e.g., via an analog-digital converter, for example, that may be a standalone component or that may be integrated within the processor. The processor 138 can be included in the wall of the housing 104 of the drug delivery device 102, as illustrated in FIG. 1B. The processor 138 can be a microprocessor that includes an arithmetic and logic unit array. The microprocessor 138 can be provided on a semiconductor substrate and interconnected to the light detection system 136 and, optionally, to the antenna 140 for executing operations on received data to generate output data, as described in detail with reference to FIG. 6. The processor 138 can be configured to determine the amount of the medicament within the drug delivery device based at least in part on the electrical signal and transmit the data including the amount of the medicament to the antenna 140 and to the display 114. In some examples, the processor 138 includes a controller configured to shift the stopper 109 position based on a dose selected by a user of the drug delivery device 102.

In some implementations, the data generated by the processor 138 is transmitted to the antenna 140. The antenna 140 can be included in the wall of the housing 104 of the drug delivery device 102, as illustrated in FIG. 1B. The antenna 140 can be a near-field communication (NFC) antenna. The antenna 140 can be configured to harvest energy for the power source 132. The antenna 140 can be configured to transmit signals to the microprocessor 138 and to an external processor. The signals transmitted by the antenna 140 can include the amount of the medicament in the medicament reservoir 106, one or more additional characteristics of the medicament (e.g., temperature) measured by the sensor 142, and the identifier of the medicament amount detection system 103 during the usage of the drug delivery device (102). The antenna 140 can be configured to transmit data, e.g., at a data rate of 106 kb/s, 212 kb/s or 424 kb/s using a technique such as Manchester bit encoding and OOK load modulation at 846 kHz.

In some implementations, the drug delivery device 102 is within an NFC field 152 that can be generated by an interrogator 154. The interrogator 154 can be separated from the external device 150 (FIG. 1B) or can be a module integrated within the external device 150. The interrogator 154 can include a signal generator 156 (e.g., RF module), a transmitter 158, a receiver 160, and a processor 162. In the implementations in which the interrogator 154 is separated from the external device 150, the interrogator 154 can be configured to transmit the data received from the drug delivery device 102 to the external device 150. The external device 150 is configured to process and display the data (e.g., medicament amount) associated with the drug delivery device 102.

FIGS. 2A-2F illustrate examples of medicament reservoirs 106, such as cartridges, for drug delivery devices, e.g., with multiple types of sealing systems 202, 212, 222, 232, and 242. The medicament reservoir 106 includes a cavity 204, a distal end 206 and a proximal end 208. The distal end 206 can be sealed by the plunger head 108b. The proximal end 208 includes an aperture 149 that can be sealed by the sealing system 200, 212, 222, 232. The sealing system 200, 212, 222, 232 can be included in or attached to the proximal end 208 as a closure. The medicament reservoir 106 is configured to allow the proximal end 208 to be securely attached (e.g., through a push mechanism, a twist mechanism or a combination of the two mechanisms) to the injection needles 122 (see FIGS. 1A-1F) such that unintentional detachment is prevented during the operation of the drug delivery device 102. The proximal end 208 typically includes a thread 203 to provide a secure connection for connecting an injection needle.

The sealing system 200, 212, 222, 232 is configured to maintain a liquid tight seal between the cavity 204 and the injection needles 122. The liquid tight seal generated by the sealing system 200, 212, 222, 232 enables that substantially all (e.g., more than 99%) of the medicament expelled by the drug delivery device 106 is expelled through the injection needles 122. The liquid tight seal generated by the sealing system 200, 212, 222, 232 increases the accuracy of a medicament amount detection system based on a stopper position, as described with reference to FIGS. 1A-1F, by eliminating unaccounted medicament leaks. The sealing system 200, 212, 222, 232 can prevent contamination of the medicament stored in the cavity 204. The sealing system 200, 212, 222, 232 can include a unidirectional valve that enables flow from the cavity 204 to the injection needles 122 and prevents flow from the injection needles 122 to the cavity 204. The sealing system 200, 212, 222, 232 can be aligned with a central longitudinal axis of the drug delivery device 106. As a difference to traditional cartridges that are closed and sealed at their proximal end by a crimp cap (including a rubber seal and a metal crimp element), the sealing system 200, 212, 222, 232 has the advantage of reducing part count, manufacturing complexity, and manufacturing cost. The sealing system 200, 212, 222, 232 is easier to produce than crimp caps.

Figure 2A:
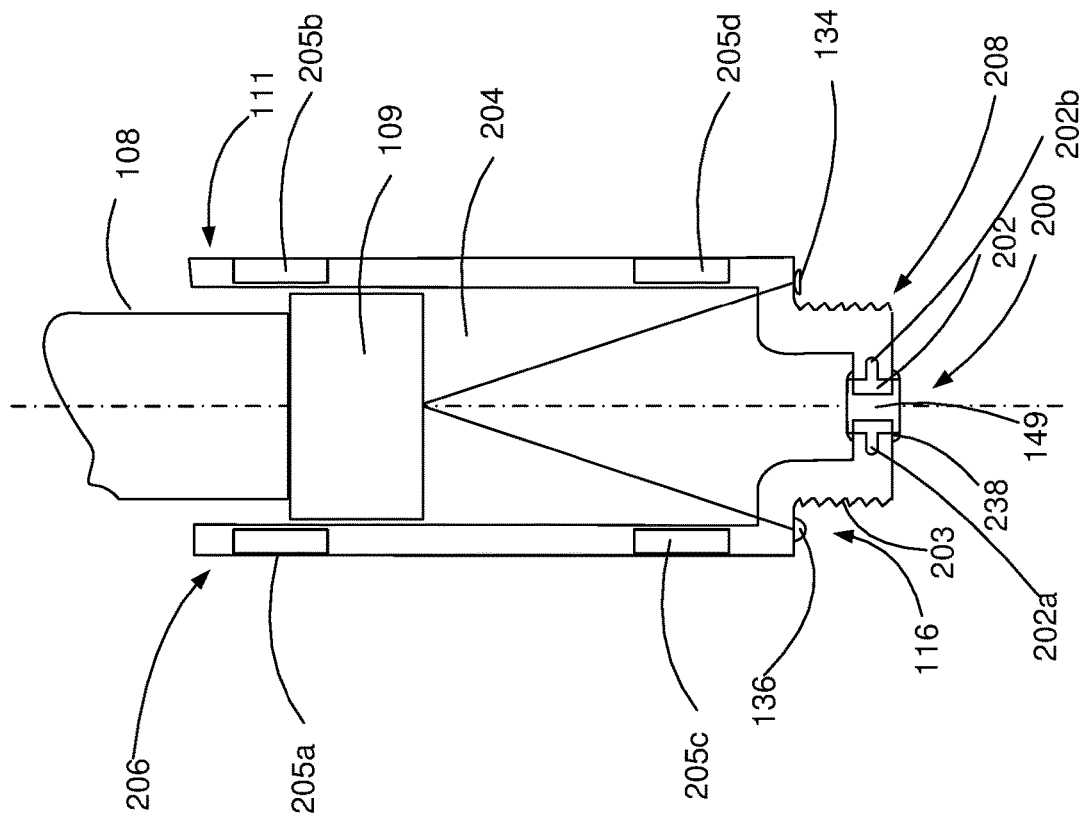
FIGS. 2A-2F are cross-sectional views of examples of devices in accordance with the present disclosure.
Figure 2B:
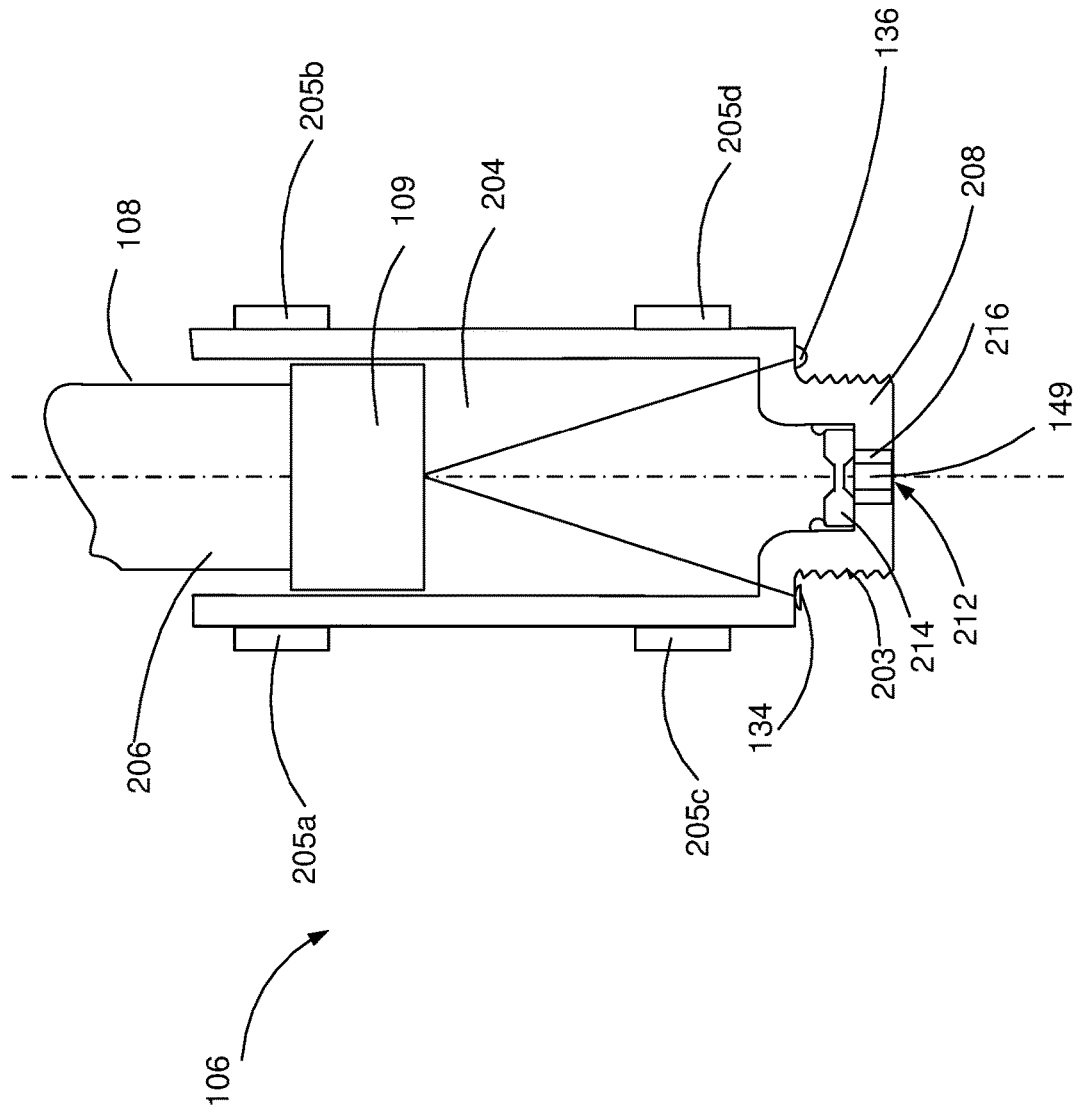
Figure 2C:
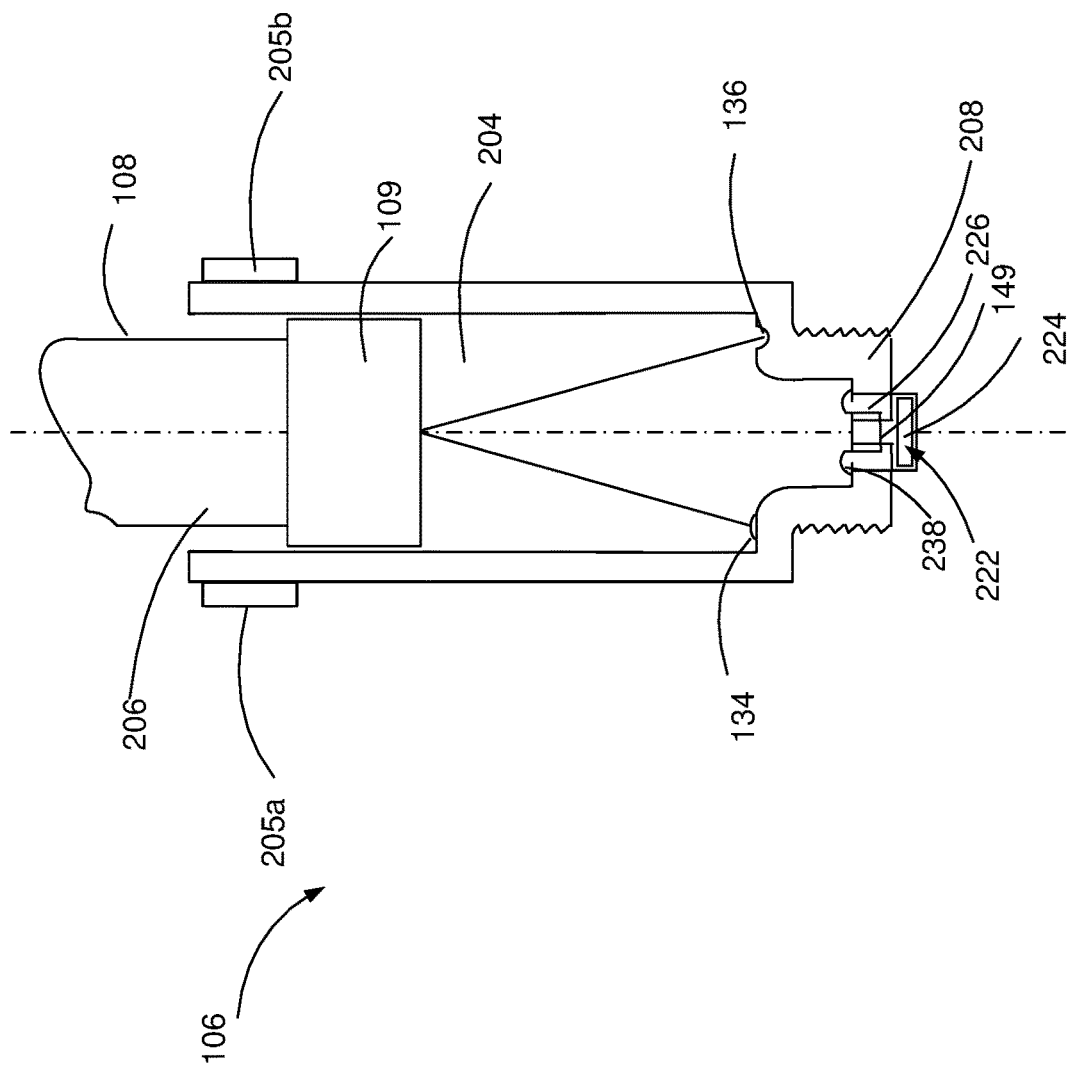
Figure 2D:
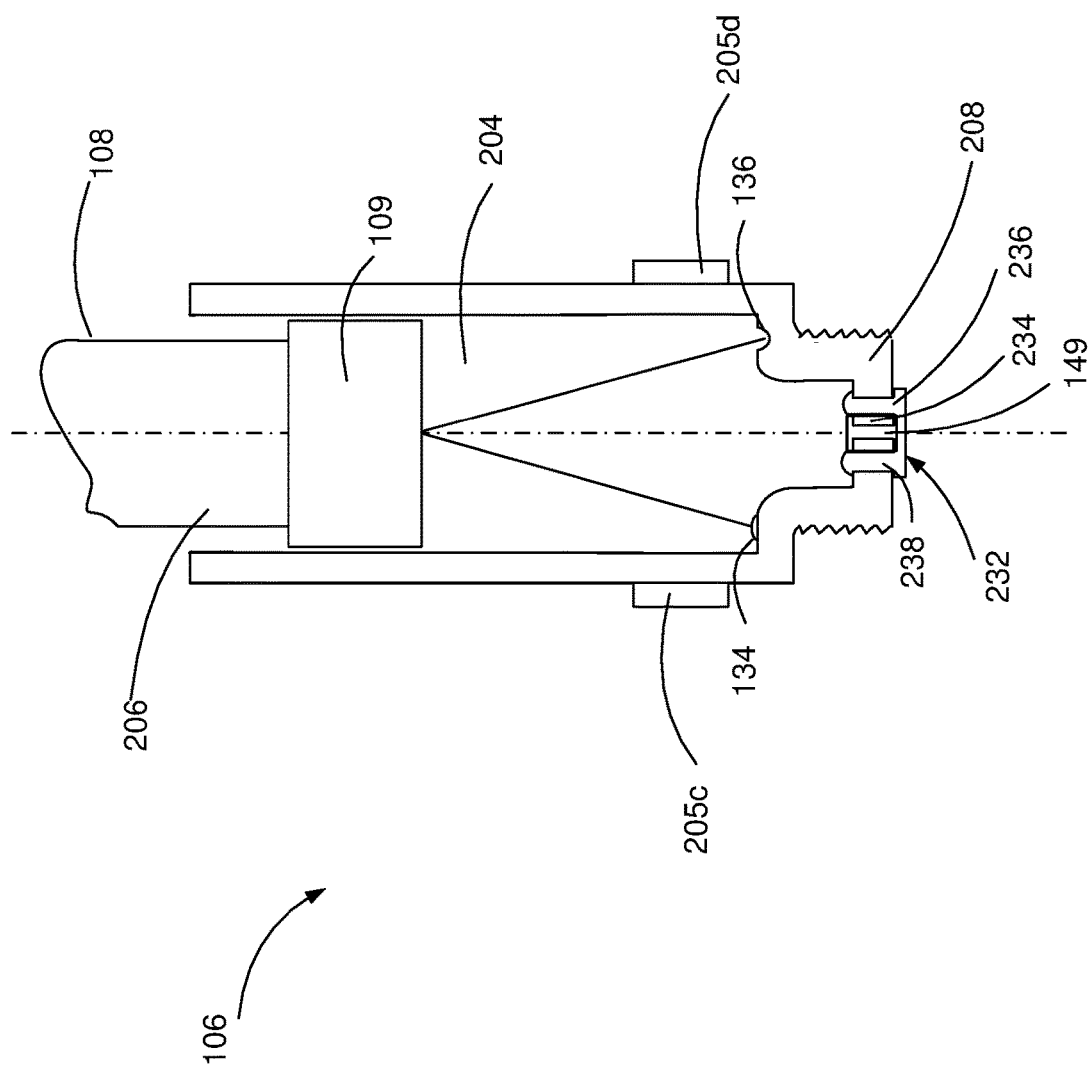

The sealing system 200, 212, 222, 232 can include one or more components, such as a septum 202, 216, 224, 234 (FIGS. 2A-2F), a septum or sealing disc 214 (FIG. 2B), and a septum carrier 226, 236 (FIGS. 2C and 2D). One or more components of the sealing system 200, 212, 222, 232 are fabricated from materials selected from a group of medical grade of plastic, silicon oxide coated plastic, thermoplastic elastomers, rubber elastomers and a combination thereof. At least one component of the sealing system 200, 212, 222, 232, such as the septum 202, 214, 224, 234 (FIGS. 2A-2F) and/or the sealing disc 214 (FIG. 2B) are fabricated from thermoplastic elastomers or rubber elastomers to form a liquid tight seal. The septum carrier 226, 236 (FIGS. 2C and 2D) can be fabricated from a material or combination of materials that enable and optimize the attachment of the septum carrier 226, 236 to the proximal end 208.

The sealing system 200, illustrated in FIG. 2A, includes a septum 202 that is insert molded or 2k-molded to seal the proximal end 208 of the medicament reservoir 106 (e.g., cartridge). The septum 202 can be fabricated from a material that enables piercing by a piercing member of the injection needles 122. The material of the septum 202 can be different from the material used for the outer wall. For example, the material is particularly softer to enable a needle to pierce through the septum 202 and cross the aperture 149 to access the medicament stored in the cavity 204. The material is also resilient in the sense that once detaching an injection needle the piercing hole is closed forming a liquid tight seal. The septum 202 has extensions 202a, 202b that provide for connecting the septum and the cartridge material and help fixing the septum at a particular position. In some implementations, the material of the sealing system 200 is melted together with the medicament reservoir 106. The septum 202 can have a lateral diameter larger than a diameter of a piercing member of the injection needles 122 and larger than the aperture 149.

The sealing system 212, illustrated in FIG. 2B, includes a septum 216 and a sealing disc 214 configured to seal the aperture 149. The septum 216 and/or the sealing disc 214 are configured to form a liquid tight seal. The septum 216 and/or the sealing disc 214 can have a thinner cross-sectional thickness for ease of piercing by the piercing member of the injection needles 122. The septum 216 can be fitted between the sidewalls of the proximal closure 208, near to the distal end of the proximal end 208, against the aperture 149. The fit may be form fit, positive fit, force closure, closed linkage, or any combination thereof. Proximal end 208 can have a retention feature (e.g., an undercut) to secure the sealing disc 214 in its position. The undercut can be an annular rib or can include a multitude of protrusions, e.g. two, three, or four protrusions, as retention features. The septum 216 can be attached to the proximal end 208 prior to filling the cavity 204 with the medicament. The septum 216 or the sealing disc 214 can be molded in the proximal end 208 by a multi-component injection molding process. In some implementations, the sealing disc 214 can be fabricated from a material that enables piercing by a piercing member of the injection needles 122, such that the material of the septum 214 is different from the material used for the outer wall. In some implementations, the sealing disc 214 can have a narrow section in the center to improve pierceability. The diameter of the narrow section does not exceed the diameter of the bore, to ensure having a liquid tight sealing.

The sealing system 222, illustrated in FIG. 2C, includes a septum 224 attached to the proximal end 208 using a septum carrier 226. The septum carrier 226 includes an opening configured to match the geometrical characteristics of the septum 224 to enable attachment of the septum 224 to the septum carrier 226. The septum 224 is attached to the septum carrier 226 in a liquid tight manner, e.g. using adhesive (permanent glue), staking or hot staking ("heissverstemmen"), or 2k-injection molding.

The septum carrier 226 may have a bore in the center to ease piercing of the septum 224. The septum carrier 226 can include any attachment means that enable the septum 224 to be securely attached to the proximal end 208 such that the septum 224 is maintained in a liquid tight seal with the cavity 204. For example, the septum carrier 226 can include a ring shaped connector 238 with a hook-shaped structure at its end to prevent the carrier being pushed out of its position when pressure is put on the stopper inside the cartridge. In addition the hook-shape end provides an annular contact area with inside surface of the proximal end 208 to ensure a liquid tight sealing. The hook-shape end also is chamfered to ease insertion of the carrier during assembly. The configuration of the sealing system 222 enables secure and liquid tight attachment to an outer surface of the proximal end 208. Similar to the embodiment described before with reference to FIG. 2B, the proximal end 208 has an aperture 149, which is sealed by the sealing system 222.

The sealing system 232, illustrated in FIG. 2D, is similar to the sealing system 222 described with reference to FIG. 2C. The sealing system 232 includes a septum 234 and a septum carrier 236 configured to form a single component. The septum 234 and the septum carrier 236 are attached to the proximal end 208, such that the septum 234 covers the aperture 149 of the proximal end 208. The septum carrier 236 can include any attachment means that enable the septum 234 to be securely attached to the proximal closure 208 such that the septum 234 is maintained in a liquid tight seal with the cavity 204. In some implementations, the attachment means include an annular ring with hook-shaped end as described with reference to FIG. 2C.

Figure 2E:
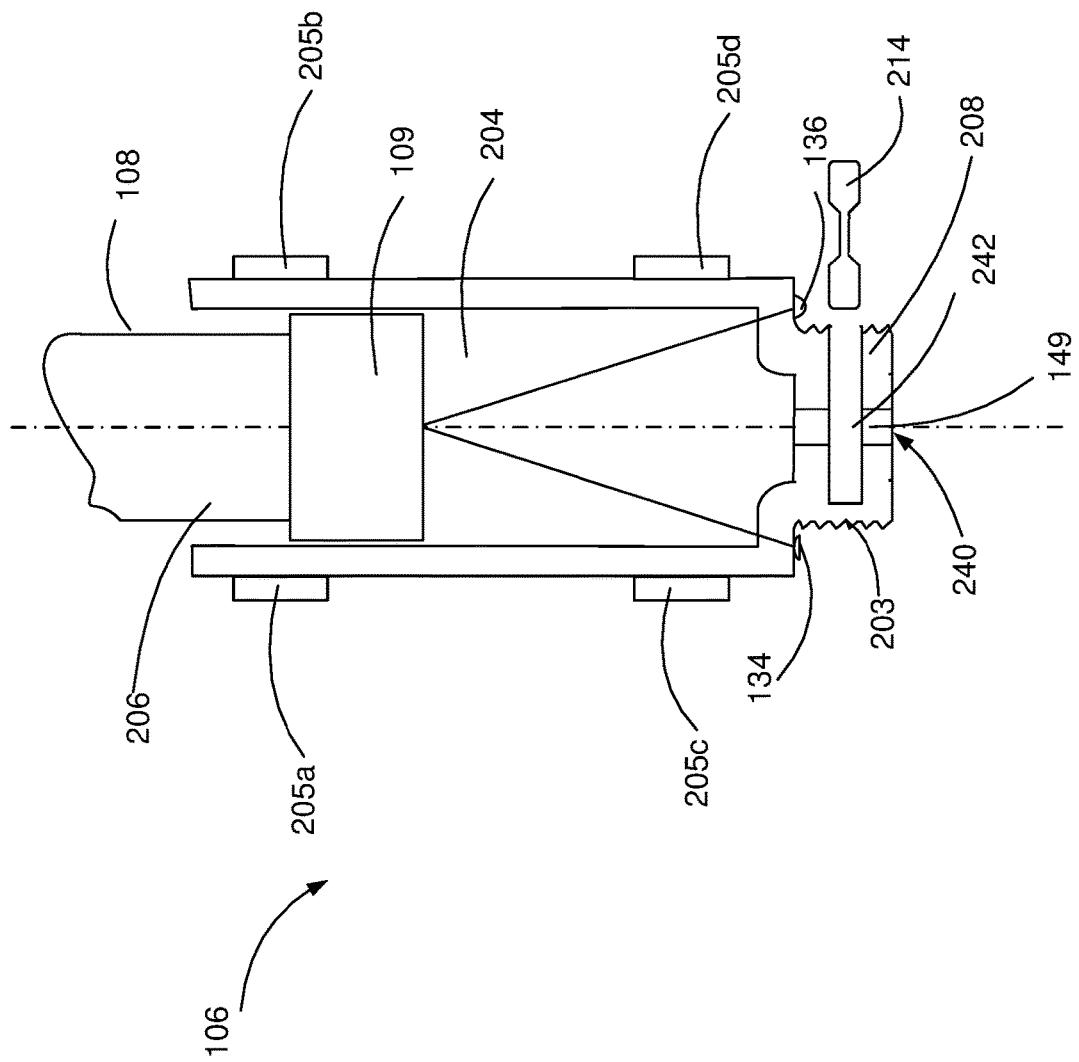
Figure 2F:
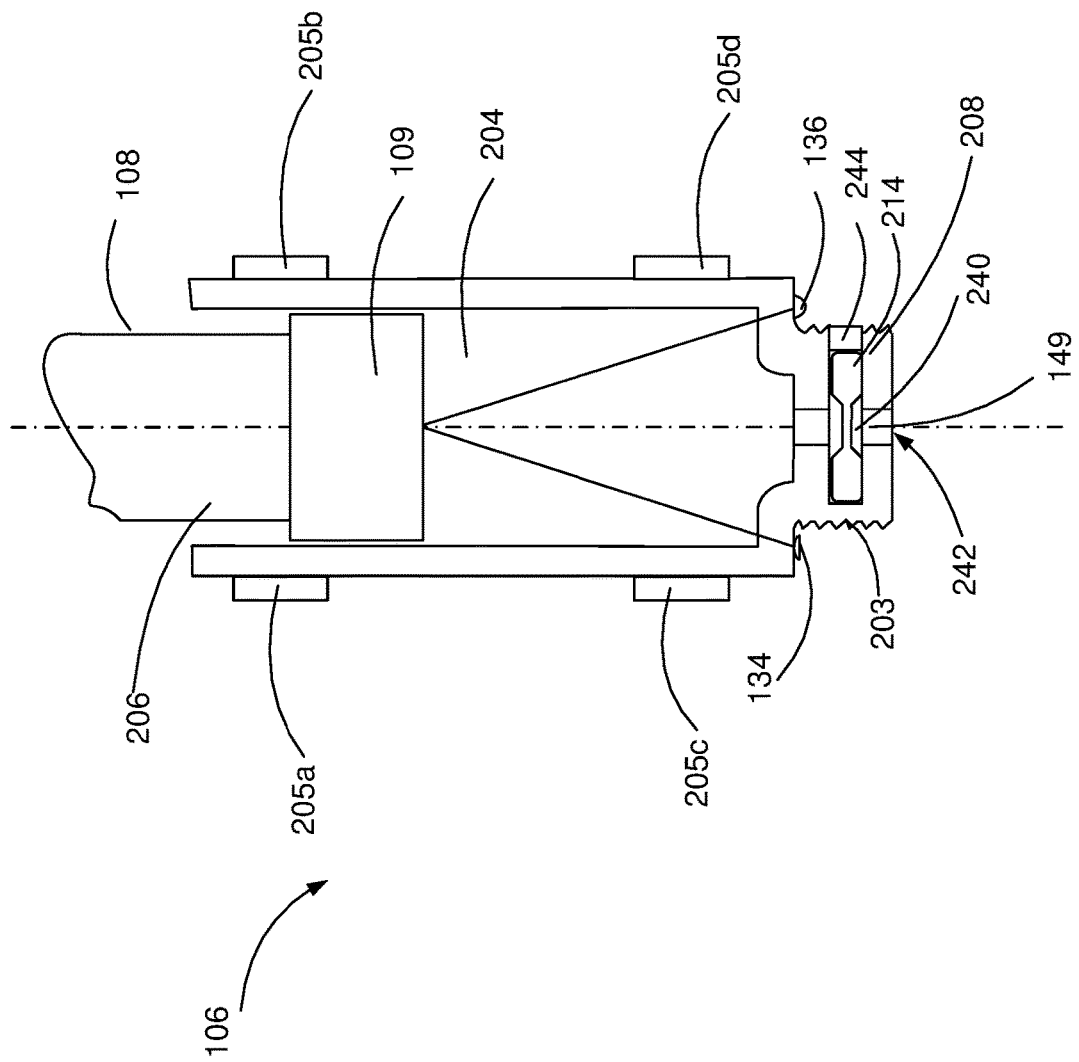

The sealing system 242, illustrated in FIGS. 2E and 2F, includes a septum 216 and a septum pocket 240 configured to seal the aperture 149. The septum 216 can be made of a rubber or customized foam, which is compressed prior to or during assembly. The compression can be supported through a cool temperature or a customized composition material of the septum 216, which is configured to form a liquid tight seal. The septum 216 can be fitted between the inner walls of the septum pocket 240. The fit may be form fit, positive fit, force closure, closed linkage, or any combination thereof. In some implementations, the septum pocket 240 can include an opening that enables insertion of the septum 216. The opening of the septum pocket 240 can be closed after the septum 216 is fitted within the septum pocket by a closing feature 244. The septum 216 can have a thinner cross-sectional thickness for ease of piercing by the piercing member of the injection needles 122. The diameter of the narrow section does not exceed the diameter of the bore, to ensure having a liquid tight sealing.

The sealing systems 200, 212, 222, 232, 242, described with reference to FIGS. 2A-2E can be included in any type of medicament reservoir 106.

The medicament reservoir 106 can include an interface 205a, 205b, 205c, 205d. In some implementations, the interface 205a, 205b can be included in or attached to the wall of the medicament reservoir 106, such that the thickness of the wall of the medicament reservoir 106 can vary in the longitudinal direction, as illustrated in FIGS. 2A-2F. In some implementations, the interface 205a, 205b can be proximal to a distal end 111, as illustrated in FIGS. 2A-2C, 2E, and 2F. In some implementations, the interface 205c, 205d can be included in or attached to the wall of the medicament reservoir 106 by a proximal end 116, as illustrated in FIGS. 2A, 2B, 2D, 2E, and 2F.

The interface 205a, 205b, 205c, 205d can be configured to ensure an accurate positioning of the medicament reservoir 106 (cartridge) relative to the medicament amount detection system 103 (e.g., optical system). For example, the interface 205a, 205b, 205c, 205d can include a circumferential groove around the outside perimeter of the wall of the medicament reservoir 106 or a blind hole with a tapered opening. The interface 205a, 205b, 205c, 205d can be configured to provide an anti-rotation lock. For example, the interface 205a, 205b, 205c, 205d can include a series of tabs or features spaced around the outside perimeter of the wall of the of the medicament reservoir 106, with corresponding grooves or features in the inner diameter of the housing 104. The interface 205a, 205b, 205c, 205d can be used to identify a particular cartridge type and/or medicament to prevent a mismatch between the medicament and the drug delivery device 102 (coding or dedication). For example, the interface 205a, 205b, 205c, 205d can include a circumferential web or other drug dedicated design solutions.

Figure 3A:
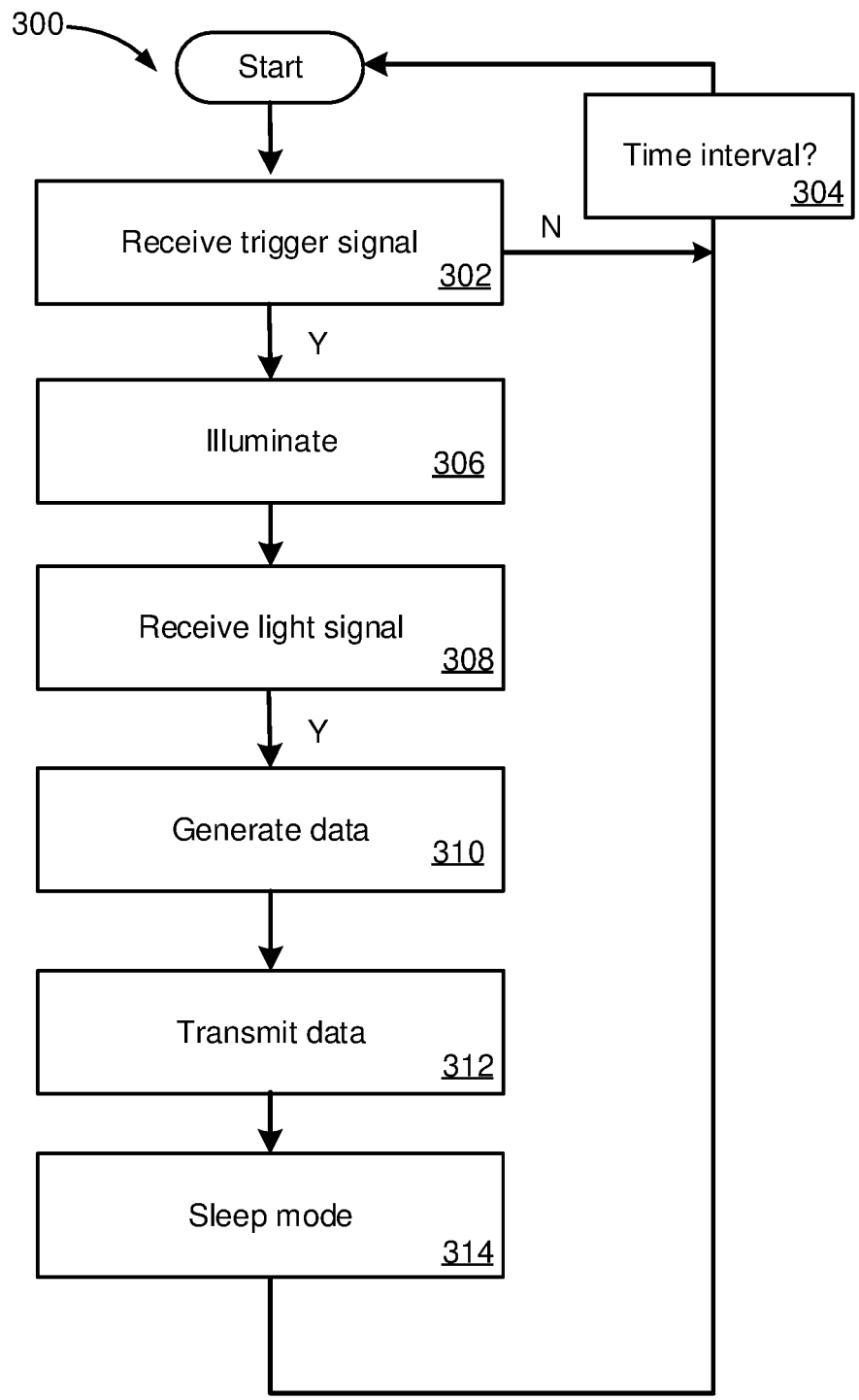
FIGS. 3A-3C are flowcharts illustrating example processes that can be executed to detect and transmit drug delivery device-level data.
Figure 3B:
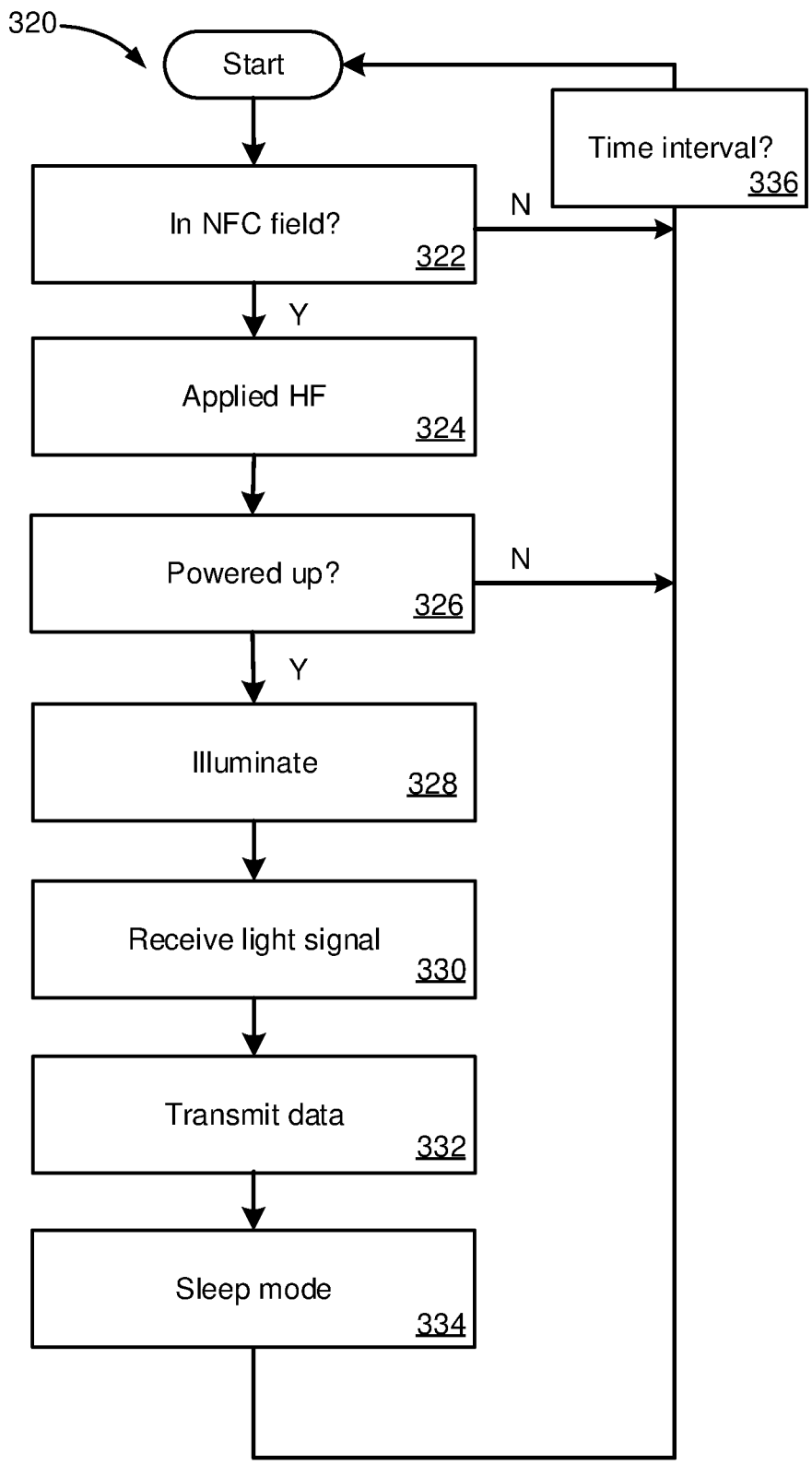
Figure 3C:
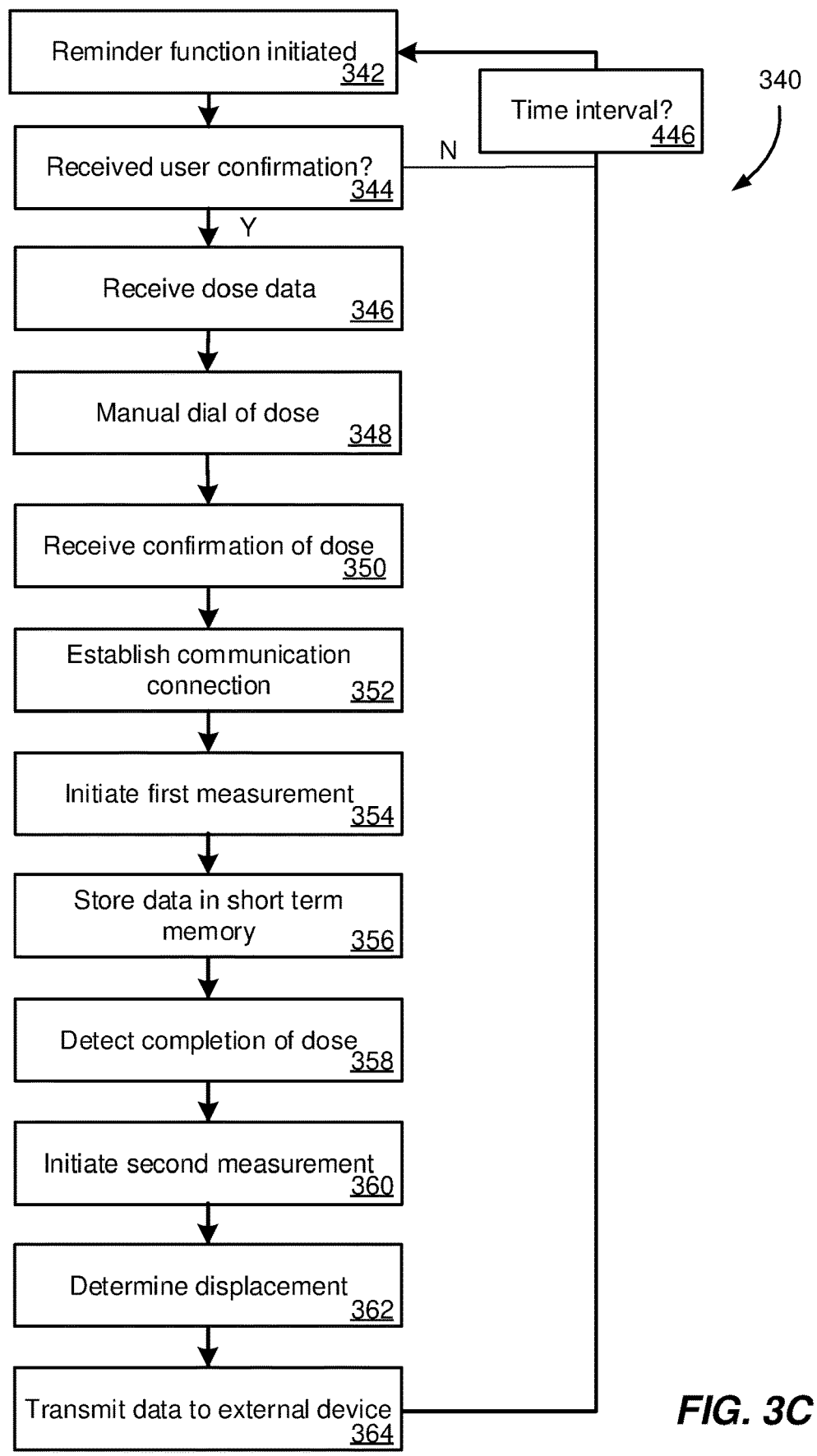

FIGS. 3A-3C are flowcharts illustrating example processes 300, 320, and 340 that can be executed to determine medicament amount data using an optical system during an operation of a drug delivery device. The processes 300, 320, and 340 can be executed by devices and systems described with reference to FIGS. 1-2.

The process 300, illustrated by FIG. 3A, begins by receiving a trigger signal (302). The trigger signal can include a priming operation on a drug delivery device having an ultrasound probe inserted in a rigid stopper. The priming operation can be initiated by a user of the drug delivery device or a user of an external device communicating with the drug delivery device.

An example of a priming operation performed with the drug delivery device can include selecting a particular number (e.g., one or two) of units of medicament and pressing an injection button while holding the drug delivery device with the needle upwards. Another example of a priming operation performed with the drug delivery device can include pressing a priming button of the drug delivery device configured as an electric switch.

In some implementations, the trigger signal can include an interrogation signal generated by an external device. The interrogation signal can be automatically generated by the external device based on one or more conditions. The conditions can include a transmission frequency, a transmission time and/or a time interval (304). For example, a medicament treatment can be scheduled to be performed within a particular time interval, during which the external device can generate interrogation signals at a given frequency. The signal can be generated by the external device in response to a user input on the external device. For example, a user can interact with an external device to initiate a medicament dispensing service. The trigger signal can include at least one of a mechanical signal, an acoustic signal and an electric signal. The trigger signal can include a command to generate an ultrasound signal.

In response to receiving the trigger signal, a light emitting system can be powered up to illuminate an optical target (306). For example, one or more LEDS or laser diodes, can direct a light signal towards a section of a surface of a stopper of the drug delivery device, as described with reference to FIGS. 1A-1C. A light detection system including a photodiode or a light dependent resistor, can detect at least a portion of the light signal reflected by the stopper surface (308). One or more features of the reflected light signal can be indicative of an amount of medicament contained by the medicament reservoir and a state of the medicament. For example, the luminescence of the reflected signal depends on the length of the light propagation path and the reflection angle, which are indicative of the amount of medicament contained by the medicament reservoir. The luminescence of the reflected signal can depend on the refractive indices of the medicament, which can change over time, due to temperature or due to contaminants, which are indicative of the state of the medicament.

In response to receiving the reflected light signal, an electric signal can be generated by the light sensor. The electric signal can be used by a processor to generate drug delivery device data (310). The drug delivery device data can include the electric signal, a unique identifier for the drug delivery device, a property of the medicament (e.g., a descent rate of a sediment within the medicament, density, optical absorption coefficients and/or temperature of the medicament), a sensor measurement (e.g., a medicament temperature), an internal clock measurement (e.g., a timestamp of receipt of the ultrasound signal), a medicament identifier, a match between medicament volume, a location, and/or a situation specific data for the drug delivery device.

The medicament temperature can be determined for medicaments including an additive or sediments based on the light signal detected by the light detection system and known descent rate of the sediments. The amount of the medicament within the drug delivery device can be determined based on one or more characteristics of the light signal detected by the light detection system. For example, the position of the stopper can be determined based on a phase of the reflected light signal using a particular detection method. The detection method can include an interferometric distance detection method and/or a phase modulation method combined with known geometrical characteristics (e.g., area of cross-section) of the drug delivery device and medicament reservoir. In some implementations, the amount of the medicament within the drug delivery device can be determined based on differential measurements associated with an initial position of the plunger (prior to dispensing the medicament) and a final position of the plunger (after dispensing the medicament).

The insertion of the correct drug in the drug delivery device can be determined based on the light signal detected by the light detection system and a comparison between determined optical absorption coefficients and known optical absorption coefficients of medicaments. The match between medicament volume and available medicament volume can be determined based on the light signal detected by the light detection system and optical absorption coefficients of medicaments versus air. The match between medicament volume and available medicament volume can be used to confirm that the medicament reservoir is not empty or partially empty. The medicament temperature can be determined for medicaments including an additive or sediments based on the light signal detected by the light detection system and known descent rate of the sediments.

An antenna of the drug delivery device can be configured to transmit the data to an external device to analyze one or more parameters associated with the administration of the medicament and the operational conditions of the drug delivery device (312). The drug delivery device data can be transmitted using radio frequency (RF) communication, a bluetooth communication, a millimeter wave communication or any other type of short-range communications. The drug delivery device data can be processed by a processor of the external device to generate result data. In response to obtaining result data, the result data can be stored for future references and displayed through a graphical user interface of the external device. In some implementations, in response to successful transmission of data, the drug delivery device can initiate a sleep mode to conserve the energy of the power source (314). In some implementations, the drug delivery device is configured to periodically restart the process based on a preset time interval (316).

The process 320, illustrated by FIG. 3B, begins by identifying whether a drug delivery device is within a communication (NFC) region (322). For example, the drug delivery device can be configured to periodically verify its proximity to the NFC region. The drug delivery device can include one or more components configured to verify the proximity of the drug delivery device to the NFC region. In some implementations, a user (e.g., a healthcare provider or a patient) can swipe the drug delivery device over the external device to generate a signal indicating entrance of the drug delivery device within the communication range (e.g., NFC region or Bluetooth field). A healthcare provider can store and use the drug delivery device while being within a medical facility configured to be within the NFC region.

In response to determining that the drug delivery device is within the NFC region, the drug delivery device determines whether a high frequency signal is applied (324). In some implementations, a high frequency signal is automatically generated in response to a usage of the drug delivery device. For example, a high frequency signal is automatically generated after the drug delivery device was used to inject an amount of the medicament contained within the drug delivery device.

In response to determining that the high frequency signal is applied the drug delivery device can be powered up (326). For example, in preparing to generate data associated with the drug delivery device, one or more electronic components of the drug delivery device are energized (as described with reference to FIGS. 1A-1C) using a power source integrated within the drug delivery device or by harvesting energy from the external device. For example, if the power source is depleted of energy, the power source can recharge while the drug delivery device is in the NFC region by harvesting energy from the external device.

In response to one or more components of the drug delivery device being powered up, a light source, such as one or more LEDS or laser diodes, can direct a light signal towards a stopper of the drug delivery device (328), as described with reference to FIGS. 1A-1C. In some implementations, the light source may be configured to continuously generate light signals during dose administration. In some implementations, the light source may be configured to periodically generate light signals at every few seconds, e.g. 1, 3, 10, or 20 seconds. Intermittent generation of light signals may be implemented to improve battery life.

A light detection system, such as a photodiode or a light dependent resistor, can detect at least a portion of the light signal reflected by the stopper and generate data associated with the detected portion of the light signal (330). The light detection system can be powered synchronously with the light source, such that each reflected light signal can be detected by the light detection system. The detection method can be based on interferometric distance detection and/or phase modulation methods, which estimate the stopper position with an accuracy of approximately 10 nm. The phase modulation method is an optical technique for measuring distances using a laser beam as a light source. The laser beam has sinusoidally modulated optical power. The laser beam is directed towards a target (e.g., a lens of the stopper). The reflected light (e.g., by the lens of the stopper) is detected and recorded. The phase of the power modulation of the reflected light is compared with the phase of the power modulation of the light source. The phase shift obtained is $2\pi$ times the time of flight times the modulation frequency. The selection of modulation frequencies affects the spatial resolution of the estimated distance such that higher modulation frequencies can result in a higher spatial resolution.

The data can include, the amount of medicament stored within the drug delivery device, a property of the medicament (e.g., density, optical absorption coefficients and/or temperature of the medicament), the insertion of the correct drug in the drug delivery device, a match between medicament volume and available medicament volume, medicament temperature and/or other data. The amount of the medicament within the drug delivery device can be determined based on the light signal detected by the light detection system and known geometrical characteristics (e.g., area of cross-section) of the drug delivery device and medicament reservoir.

The insertion of the correct drug in the drug delivery device can be determined based on the light signal detected by the light detection system and a comparison between determined optical absorption coefficients and known optical absorption coefficients of medicaments. The match between medicament volume and available medicament volume can be determined based on the light signal detected by the light detection system and optical absorption coefficients of medicaments versus air. The match between medicament volume and available medicament volume can be used to confirm that the medicament reservoir is not empty or partially empty. The medicament temperature can be determined for medicaments including an additive or sediments based on the light signal detected by the light detection system and known descent rate of the sediments.

The drug delivery device can be configured to transmit the data to a database, such as central database 412 described with reference to FIG. 4B (332). In response to successful transmission of data, the drug delivery device can initiate a sleep mode to conserve the energy of the power source (334). In some implementations, a user (e.g., a healthcare provider or a patient) can swipe the drug delivery device over the external device to generate a signal that initiates a sleep mode. In some implementations, the drug delivery device is configured to periodically restart the process based on a preset time interval (336).

The process 340, illustrated by FIG. 3C, begins by initiating a reminder function on an external device (342). The reminder function can be an application that generates audio, haptic, and/or visual alerts on the external device. The reminder function can enable a user to select reminders and alert types based on a treatment schedule. The treatment includes delivery of a medicament dose with a drug delivery device.

In response to the alert of the reminder function, a user can confirm initiation of treatment or can postpone the treatment with a particular time interval (344). If the user confirms initiation of treatment, a dose of medicament to be injected can be selected or a preselected dose can be confirmed by a user input on the external device (346). In response to the confirmation of the dose, the user can receive an instruction to manually select the dose on the drug delivery device (348). For example, the user can select the dose on the drug delivery device by rotating a dose dial and/or pressing a dose release button. After selecting the dose, the user can generate a user input confirming setting the dose on the drug delivery device (350).

In response to the user input or in response to setting the dose, a communication between the drug delivery device and the external device can be established (352). Establishing the communication between the drug delivery device and the external device can include powering up the drug delivery device. For example, at least some of the electronic components of the drug delivery device including a light source (e.g., LEDS or laser diodes) and a light detection system (e.g., a photodiode or a light dependent resistor) are energized.

Energizing the electronic components of the drug delivery device can initiate a first measurement (354). The first measurement can include generating and directing, by the light emitting system, a light signal towards a portion of a stopper of the drug delivery device (e.g., lens of the stopper), detecting, by the light detection system, a reflected signal, and determining a first position of the stopper. The first position of the stopper can be determined using an interferometric distance detection method and/or a phase modulation method. The determined data including the first position of the stopper and, optionally, one or more environmental sensor data (e.g., temperature, humidity and luminosity) can be stored in a short-term memory (356).

After expelling the set dose of medicament, a signal is generated to indicate completion of treatment (358). For example, the signal can be generated in response to a user activating a power off switch. Powering off may include a time delay to initiate a second measurement (360). The second measurement can include generating and directing, by the light source, a light signal towards a portion of a stopper of the drug delivery device (e.g., lens of the stopper), detecting, by the light detection system, a reflected signal, and determining a second position of the stopper. A processor of the drug delivery device can receive the value of the second position of the stopper and the value of the first position of the stopper to determine displacement of the stopper (362). Drug delivery device data including the displacement of the stopper and one or more environmental sensor data (e.g., temperature, humidity and luminosity) are transmitted, by an antenna of the drug delivery device, from the drug delivery device to the external device (364). In response to successful transmission of the drug delivery device data, the drug delivery device can initiate a sleep mode to conserve the energy of the power source. In some implementations, the drug delivery device is configured to periodically restart the process 320 based on a preset time interval (366).

Figure 4:
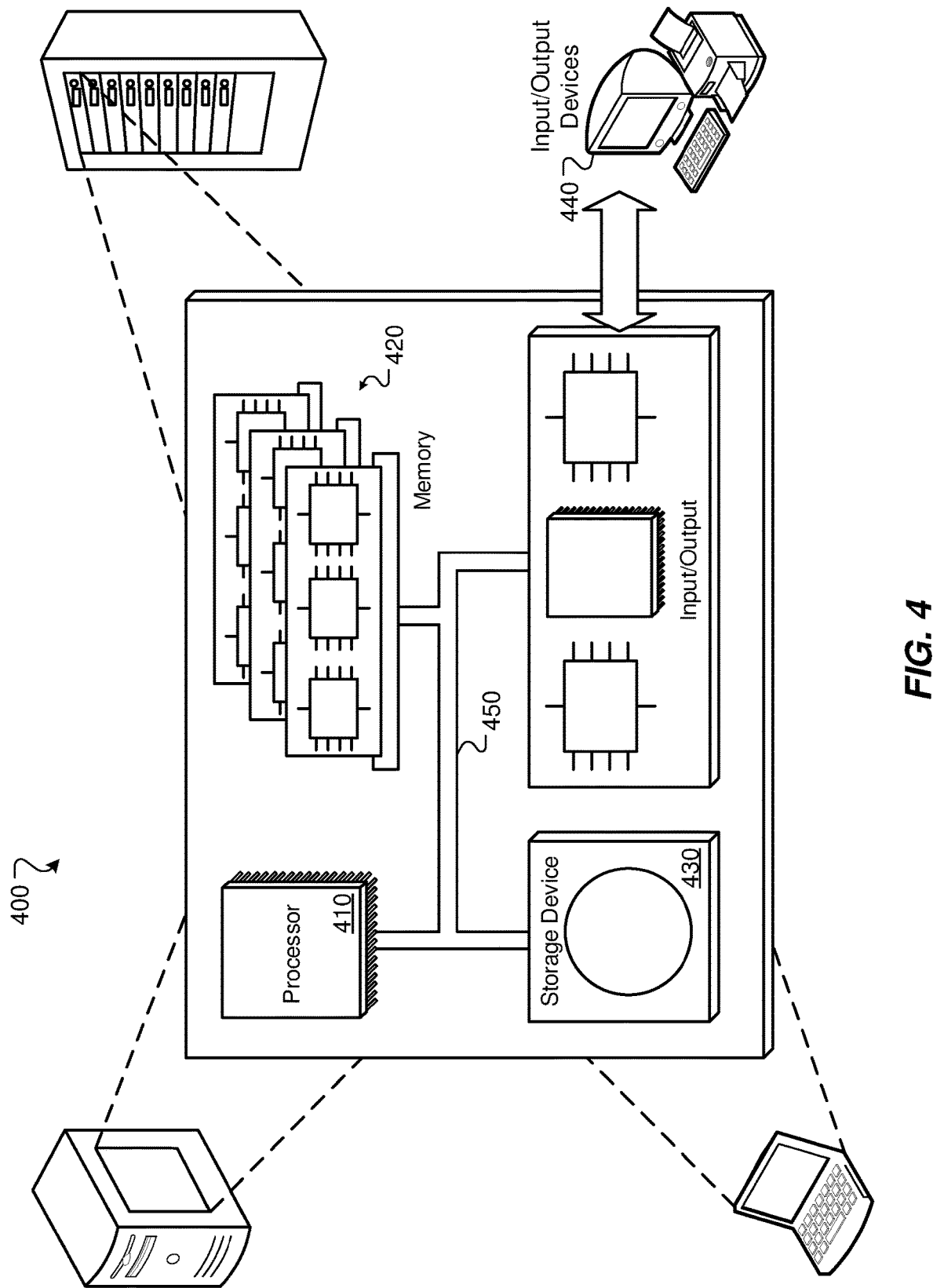
FIG. 4 is a schematic illustration of example computer systems that can be used to execute implementations of the present disclosure.

Referring now to FIG. 4, a schematic diagram of an example computing system 400 is provided. The system 400 can be used for the operations described in association with the implementations described herein. For example, the system 400 can be included in any or all of the server components discussed herein. The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit. The storage device 430 is capable of providing mass storage for the system 400. In one implementation, the storage device 430 is a computer-readable medium. In various different implementations, the storage device 430 can be a floppy disk device, a hard disk device, an optical disk device, or a tape device. The input/output device 440 provides input/output operations for the system 400. In one implementation, the input/output device 440 includes a keyboard and/or pointing device. In another implementation, the input/output device 440 includes a display unit for displaying graphical user interfaces that enable a user to access data related to a drug delivery device that is collected, stored and queried as described with reference to FIGS. 1-5.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other implementations are within the scope of the following claims.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides.

Nucleic acids may be incorporated into molecular delivery systems such as vectors, plasmids, or liposomes. Mixtures of one or more of these drugs are also contemplated.

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin.

Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immuno-pharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

A number of implementations of the present disclosure have been described. Nevertheless, it will be understood that various modifications can be made without departing from the spirit and scope of the present disclosure.

Accordingly, other implementations are within the scope of the following claims.

REFERENCE NUMERALS 100 medicament system
102 drug delivery device
103 medicament amount detection system
104 medicament container housing
106 medicament reservoir
107 longitudinal axis
108 plunger
108a plunger rod
108b a plunger head
109 stopper
109a surface of the stopper
110 injection button
111 distal end
112 dosage knob
114 dosage window
115 wall
116 proximal end of wall portion
117 proximal end of wall portion
118 nose piece
120 display window
122 needle
124 handle
126 inner needle cap
128 outer needle cap
130 cap
132 power source
134 light emitting system
136 light detection system
138 processor
140 antenna
142 sensor
144 insert
146 lens
148 sealing component
149 aperture
150 external device
152 near-field communication field
154 interrogator
156 signal generator
160 receiver
200 sealing system
202 septum
204 cavity
206 distal end
208 proximal end
212 sealing system
214 sealing disc
216 septum
222 sealing system
224 septum 226 septum carrier
232 sealing system
234 septum
236 septum carrier
238 connectors
300 processes
400 computing system
410 processor
420 memory
430 storage device
440 input/output device
450 system bus

What is claimed is:

1. A drug delivery device comprising:
a reservoir comprising a wall defining a proximal end and a distal end;
a stopper comprising an optically reflecting element, the stopper being configured to expel a portion of a medicament stored within the reservoir by moving within the reservoir in a direction from the distal end to the proximal end, such that a stopper position is indicative of an amount of the medicament within the reservoir;
a light emitting system being configured to emit a light signal perpendicular to a travelling direction of the stopper to allow the light signal to travel through one of a concave geometry or a convex geometry defined by a first portion of the wall of the reservoir towards the stopper from the proximal end of the reservoir; and
a light detection system being configured to detect a reflected light signal perpendicular to the travelling direction of the stopper, the reflected light signal provided by a reflection of at least a portion of the light signal on the optically reflecting element of the stopper, the reflected light signal travelling towards the proximal end of the reservoir, and through an other of the concave geometry or the convex geometry defined by a second portion of the wall of the reservoir and a light collector of the light detection system,
wherein the light collector is configured to direct the reflected light signal to a light detector of the light detection system that is configured to provide an electrical signal in response to detecting the reflected light signal.

2. The drug delivery device of claim 1, wherein at least one of the first portion of the wall or the second portion of the wall is opposite in location to an inner face of the stopper.

3. The drug delivery device of claim 1, wherein at least one of the first portion of the wall or the second portion of the wall at the proximal end is substantially optically transparent.

4. The drug delivery device of claim 1, wherein at least one of the first portion of the wall or the second portion of the wall defines a planar oblique geometry.

5. The drug delivery device of claim 1, wherein the one of the concave geometry or the convex geometry defined by the first portion of the wall is the concave geometry and the other of the concave geometry or the convex geometry defined by the second portion of the wall is the convex geometry.

6. The drug delivery device of claim 1, wherein the light emitting system is configured to emit the light signal towards a central portion of the stopper.

7. The drug delivery device of claim 1, wherein the light emitting system comprises a light emitting diode and the light detection system comprises a light dependent resistor configured to emit the electrical signal based on a brightness of the reflected light signal.

8. The drug delivery device of claim 1, wherein the light emitting system comprises a laser diode and the light detection system comprises a laser receiver sensor configured to emit the electrical signal based on an angle or a phase of the reflected light signal.

9. The drug delivery device of claim 1, wherein the optically reflecting element of the stopper comprises one of a cylinder lens or an aspherical lens.

10. The drug delivery device of claim 1, wherein the optically reflecting element is located within a central portion of the stopper.

11. The drug delivery device of claim 1, comprising a processor that is configured to process the electrical signal to determine the amount of the medicament within the reservoir.

12. The drug delivery device of claim 11, wherein the processor is configured to determine an expelled dose based on a difference between the reflected light signal detected before an injection compared to the reflected light signal detected after the injection.

13. The drug delivery device of claim 11, wherein the processor is configured to determine the amount of the medicament within the reservoir based on a phase of the reflected light signal.

14. The drug delivery device of claim 11, wherein the processor is configured to determine a property of the medicament within the reservoir.

15. The drug delivery device of claim 1, wherein the reservoir is made of an optically transparent plastic material comprising one of a cyclic olefin copolymer (COC) or a cyclo-olefin polymer (COP).

16. The drug delivery device of claim 1, wherein the light collector is attached to the wall of the reservoir and separated from the light detector.

17. A drug delivery system comprising:
a drug delivery device comprising:
a reservoir comprising a wall defining a proximal end and a distal end;
a stopper comprising an optically reflecting element, the stopper being configured to expel a portion of a medicament stored within the reservoir by moving within the reservoir in a direction from the distal end to the proximal end, such that a stopper position is indicative of an amount of the medicament within the reservoir;
a light emitting system attached to an outer side of the wall of the reservoir, the light emitting system being configured to provide a light signal through one of a concave geometry or a convex geometry defined by a first portion of the wall of the reservoir towards the stopper from the proximal end of the reservoir; and
a light detection system attached to the outer side of the wall of the reservoir, the light detection system being configured to detect a reflected light signal provided by a reflection of at least a portion of the light signal on the optically reflecting element of the stopper, the reflected light signal travelling towards the proximal end of the reservoir that travelled through an other of the concave geometry or the convex geometry defined by a second portion of the wall of the reservoir and a light collector of the light detection system, the light collector configured to direct the reflected light signal to a light detector of the light detection system that is configured to provide an electrical signal in response to detecting the reflected light signal; and an external device comprising:
    a receiver being configured to receive injection device data, the injection device data being based on the electrical signal in response to detecting the reflected light signal; and
    one or more processors being configured to process the injection device data and to generate result data.

18. The drug delivery system of claim 17, wherein the drug delivery device comprises a processor configured to determine the amount of the medicament within the reservoir based on the electrical signal.

* * * * *